US008628773B2

(12) United States Patent
Guo

(10) Patent No.: US 8,628,773 B2
(45) Date of Patent: Jan. 14, 2014

(54) ANTIGEN BINDING PROTEINS

(75) Inventor: Amy Y. Guo, Mercer Island, WA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 13/441,742

(22) Filed: Apr. 6, 2012

(65) Prior Publication Data

US 2012/0328511 A1     Dec. 27, 2012

Related U.S. Application Data

(60) Provisional application No. 61/473,014, filed on Apr. 7, 2011.

(51) Int. Cl.
*A61K 39/395*     (2006.01)
*C07K 16/00*      (2006.01)

(52) U.S. Cl.
USPC ................................ 424/130.1; 530/387.1

(58) Field of Classification Search
None
See application file for complete search history.

(56) References Cited

U.S. PATENT DOCUMENTS

| | | | |
|---|---|---|---|
| 4,301,144 A | 11/1981 | Iwashita | |
| 4,496,689 A | 1/1985 | Mitra | |
| 4,670,417 A | 6/1987 | Iwasaki | |
| 4,791,192 A | 12/1988 | Nakagawa | |
| 4,946,778 A | 8/1990 | Ladner | |
| 5,530,101 A | 6/1996 | Queen | |
| 5,545,807 A | 8/1996 | Surani | |
| 5,565,332 A | 10/1996 | Hoogenboom | |
| 5,585,089 A | 12/1996 | Queen | |
| 5,693,761 A | 12/1997 | Queen | |
| 5,693,762 A | 12/1997 | Queen | |
| 5,766,886 A | 6/1998 | Studnicka | |
| 5,859,205 A | 1/1999 | Adair | |
| 5,869,619 A | 2/1999 | Studnicka | |
| 5,939,598 A | 8/1999 | Kucherlapati | |
| 6,054,297 A | 4/2000 | Carter | |
| 6,072,035 A | 6/2000 | Hardman | |
| 6,075,181 A | 6/2000 | Kucherlapati | |
| 6,114,598 A | 9/2000 | Kucherlapati | |
| 6,133,426 A | 10/2000 | Gonzalez | |
| 6,150,584 A | 11/2000 | Kucherlapati | |
| 6,162,963 A | 12/2000 | Kucherlapati | |
| 6,180,370 B1 | 1/2001 | Queen | |
| 6,235,883 B1 | 5/2001 | Jakobovits | |
| 6,660,843 B1 | 12/2003 | Feige | |
| 7,202,343 B2 * | 4/2007 | Gudas et al. ............... | 530/387.1 |
| 7,807,798 B2 | 10/2010 | Jakobovits | |
| 2003/0093820 A1 | 5/2003 | Green | |
| 2007/0048754 A1 | 3/2007 | Freeman | |
| 2007/0087394 A1 | 4/2007 | Siena | |
| 2008/0031801 A1 | 2/2008 | Lackner | |
| 2008/0112848 A1 | 5/2008 | Huffstodt | |
| 2008/0234145 A1 | 9/2008 | Mueller | |
| 2008/0293055 A1 | 11/2008 | Freeman | |
| 2009/0075267 A1 | 3/2009 | Siena | |
| 2009/0269344 A1 | 10/2009 | Siena | |

FOREIGN PATENT DOCUMENTS

| | | |
|---|---|---|
| EP | 0143949 A1 | 6/1985 |
| WO | 9634096 A1 | 10/1996 |
| WO | 9824893 A2 | 6/1998 |
| WO | 0183525 A2 | 11/2001 |
| WO | 2007006310 | 1/2007 |

OTHER PUBLICATIONS

Ab Initio Protein Structure Prediction Using a Combined Hierarchical Approach, in Proteins, Structure, Function and Genetics Suppl., 3:194-198, 1999.
Altschul et al., J. Mol. Biol. 215:403-410, 1990.
Altschul et al., Nuc. Acids Res. 25:3389-3402, 1977.
Arnon et al., Monoclonal Antibodies For Immunotargeting Of Drugs In Cancer Therapy, pp. 243-56, 1985.
Asghar et al., Clin. Colorectal Cancer, Dec. 9(5): 274-81, 2010.
Augello, J of Cellular Physiology 207:654-659, 2006.
Ausubel et al., Current Protocols in Molecular Biology, ed., John Wiley & Sons Eds. 1995 Supplement.
Bowie et al., Science, 253:164-170. 1991.
Brams et al., J. Immunol. 160: 2051-2058 ,1998.
Brenner et al., Curr. Op. Struct. Biol., 7(3):369-376 ,1997.
Capaldi et al., Biochem. Biophys. Res. Comm., 76: 425, 1977.
Carballido et al., Nat. Med., 6: 103-106, 2000.
Carillo et al., *Siam J. Applied Math.* 48:1073, 1988.
Carpenter et al. Ann Rev. Biochem. 56:881-914, 1987.
Cheung, et al., Virology 176:546-552, 1990.
Chou et al., Adv. Enzymol. Relat. Areas Mol. Biol., 47:45-148, 1978.
Chou et al., Ann. Rev. Biochemistry, 47:251-276, 1978.
Chou et al., Biochemistry, 113(2):211-222, 1974.
Chou et al., Biophysical Journal, 26:367-384, 1979.
Chowdhury & Pastan, Nature Biotech., 17: 568-572. 1999.
Co et al., Mol. Immunol., 30:1361-1367, 1993.
Cole et al., pp. 77-96 in Monoclonal Antibodies and Cancer Therapy, Alan R. Liss, Inc., 1985.
Coligan, Current Protocols in Immunology (1991); Harlow & Lane, Antibodies, A Laboratory Manual, 1988.
Creighton, Ed., W. H. Freeman et al., Proteins, Structures and Molecular Principles, New York, 1984.
Davis et al., 1986, Basic Methods in Molecular Biology, Elsevier; Chu et al., 1981, Gene 13:197.
Dayhoff et al., 1978, Atlas of Protein Sequence and Structure 5:345-352 for the PAM 250 comparison matrix.
Devereux et al., Nucl. Acid Res. 12:387; Genetics Computer Group, University of Wisconsin, Madison, WI, 1984.
Dinarello, "Proinflammatory and Anti-Inflammatory Cytokines in Rheumatoid Arthritis: A Primer for Clinicians", 3rd Edition Amgen Inc., Thousand Oaks, CA, 2001.
Douillard J et al., J of Clinicacal Oncology vol. 31(18), 2010.
Engelhard et al., Proc. Nat. Acad. Sci. (USA), 91: 3224-7,1994.
Eppstein et al., Proc. Natl. Acad. Sci. USA, 82:3688-3692, 1985.
Evans et al., J. Med. Chem., 30:1229, 1987.
Fauchere, J., Adv. Drug Res., 15:29, 1986.
Fishwild, D.M. et al., High-avidity human IgGK monoclonal antibodies from a novel strain of minilocus transgenic mice, Nature Biotechnology 14: 845-851, 1996.
Fundamental Immunology, Ch. 7, Paul, W., ed., 2nd ed. Raven Press, N.Y.. 1989.
Gennaro, Remington: The Science and Practice of Pharmacy, 20th Edition, 2003.

(Continued)

*Primary Examiner* — Michael Pak
(74) *Attorney, Agent, or Firm* — Scott N. Bernstein

(57) ABSTRACT

Antigen binding proteins, such as antibodies, that interact with Epidermal Growth Factor Receptor (EGFR) are described. Methods of treating cancers and other diseases by administering a pharmaceutically effective amount of an antigen binding protein to EGFR are also described.

13 Claims, 4 Drawing Sheets

(56) References Cited

OTHER PUBLICATIONS

Figure 1:
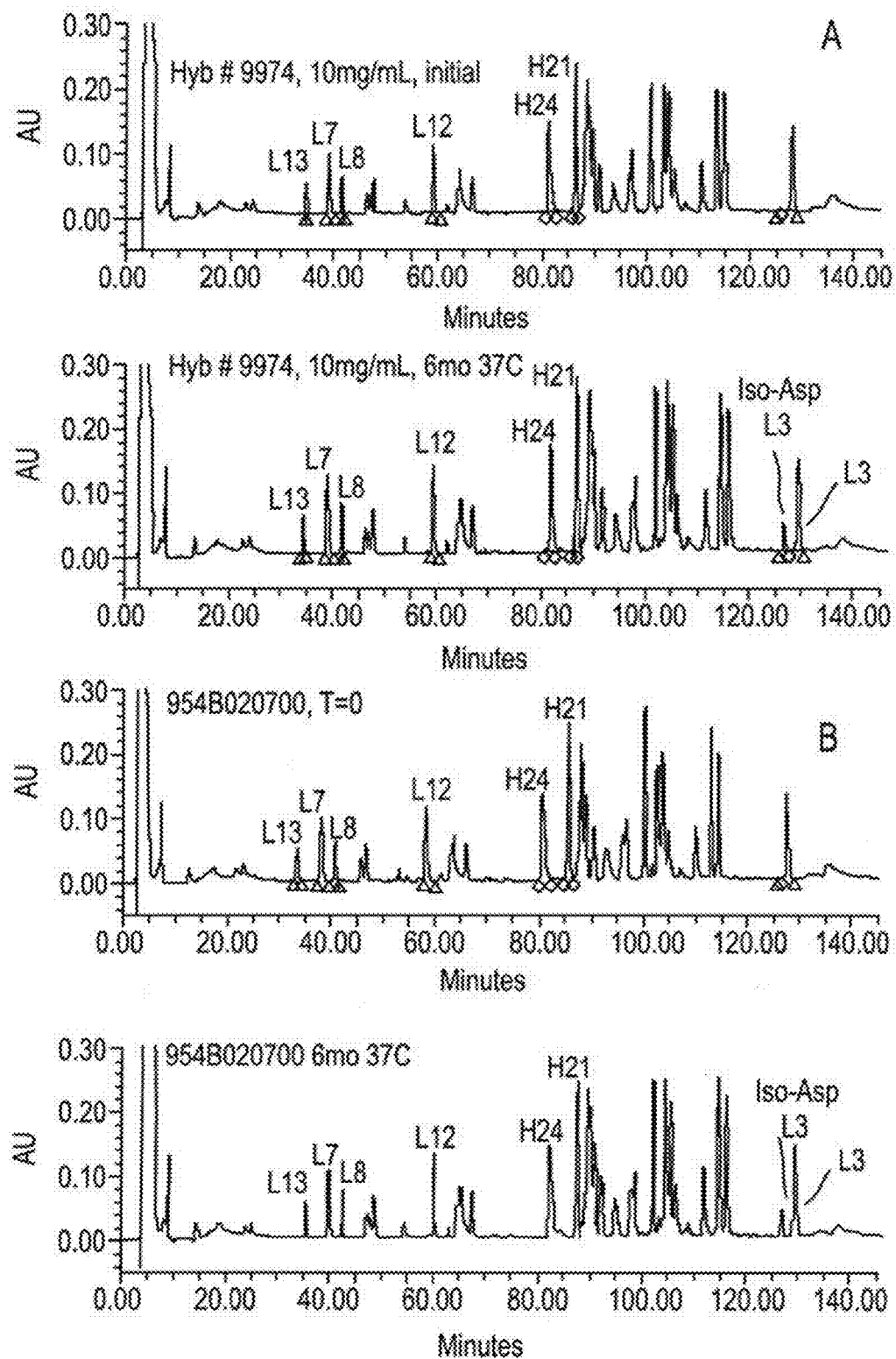

Gennaro, Remington's Pharmaceutical Sciences, 18$^{th}$ Ed., A.R., ed., Mack Publishing Company,1995.
Gilliland et al., J. Immunol., 62(6):3663-71 1999.
Goding, Monoclonal Antibodies: Principles and Practice (2d ed. 1986)).
Golub & Green, Eds, Immunology—A Synthesis (2nd Ed., Sinauer Assoc., Sunderland, Mass. 1991.
Graham et al., Virology 52:456, 1973.
Gribskov et al., Meth. Enzym., 183:146-159, 1990.
Gribskov et al., Proc. Nat. Acad. Sci. USA, 84(13):4355-4358, 1987.
Griffin, A. M., and Griffin, H. G., eds., Computer Analysis of Sequence Data, Part I, New Jersey: Humana Press, 1994.
Hellstrom et al., "Antibodies for Drug Delivery" in Controlled Drug Delivery (2nd Ed.), Robinson et al. (eds.), pp. 623-53 (Marcel Dekker, Inc. 1987).
Henikoff & Henikoff, Proc. Natl. Acad. Sci. USA 89:10915, 1989.
Henikoff et al., Proc. Natl. Acad. Sci. U.S.A. 89:10915-10919, 1992.
Hermentin and Seiler, Behring Inst. Mitt. 82:197-215, 1988.
Holm et al., Nucl. Acid. Res., 27(1):244-247 1999.
Hoogenboom et al., J. Mol. Biol., 227: 381 1991.
Hudson, Curr. Opin. Biotech., 9:395-402 1999.
Humphrey et al. PNAS (USA) 87:4207-4211 (1990.
Ifversen et al., Sem. Immunol., 8:243-248 1996.
Innis et al. (1990) PCR Protocols, A Guide to Methods and Applications, Academic Press, Inc. N.Y.).
Introduction to Protein Structure C. Branden & J. Tooze, eds., Garland Publishing, New York, N.Y. 1991.
Ishida et al., Cloning Stem Cells, 4:91-102, 2002.
Johnson & Wu, Nucleic Acids Res., 28:214-8, 2000.
Jones et al., Nature 321:522-525 1986.
Jones, D., Curr. Opin. Struct. Biol., 7(3):377-87 1997.
Kabat, Sequences of Proteins of Immunological Interest (National Institutes of Health, Bethesda, MD., 1987 and 1991.
Kirkland et al., J. Immunol. 137:3614-3619, 1986.
Kohler & Milstein, Nature 256:495-497,1975.
Kostelny et al., J. Immunol., 148:1547-1553 1992.
Kozbor et al., Immunology Today 4: 72, 1983.
Kuby, Immunol., 3$^{rd}$ ed. 1997.
Kyte et al., J. Mol. Biol., 157:105-131 1982.
Lesk, A. M., ed., Computational Molecular Biology, New York: Oxford University Press, 1988.
Langer et al., J. Biomed. Matter. Research., 15:167-277, 1981.
Langer, Chem. Tech., 12:98-105, 1982.
Lieberman, Pharmaceutical Dosage Forms vols. 1-3, 1992.
Lloyd, The Art, Science and Technology of Pharmaceutical Compounding 1999.
Lonberg & Huszar, Intern. Rev. Immunol. 13:65-93 1995.
Lonberg et al., Nature, 368:856-859 1994.
MacCallum et al., J. Mol. Biol., 5:732-45 1996.
Maniatis et al., in Molecular Cloning: A Laboratory Manual, Cold Spring Harbor Laboratory, New York, 1982.
Marks et al., Bio/Technology 10:779-783, 1992.
Marks et al., J Mol Biol. 222: 581, 1991.
Martensson et al., Immunol., 83:1271-179, 1994.
Martensson et al., Immunol., 84: 224-230 1995.
Martin et al., Proc. Natl. Acad. Sci. (USA), 86:9268-9272, 1989.
McCafferty et al., Nature 348:552-554, 1990.
McCune et al., Science, 241:1532-1639 1988.
Mendelsohn, *Cancer Biology* 1:339-344, 1990.
Mendelsohn, *Cancer Cell*, 7:359, 1989.
Mendez et al., Nature Genetics, 15:146-156, 1997.
Modjtahedi and Dean Int'l, *J Oncology* 4:277-296, 1994.
Moldenhauer et al., Scand. J. Immunol. 32:77-82, 1990.
Morel et al., Molec. Immunol. 25:7-15, 1988.
Morrison, Nature, 368:812-13, 1994.
Mosier et al., Nature, 335:256-259, 1988.
Moult J., Curr. Op. In Biotech., 7(4):422-427, 1996.
Mullinax et al., Proc Natl Acad Sci (USA), 87(20): 8095-8099, 1990.
Murphy et al., Blood, 86:1946-1953, 1995.
Nascimento, George: Biochemistry, LNKD-PUBMED: 2271602; V. 29, No. 41, 1990.
Needleman & Wunsch, *J. Mol. Biol.* 48:443, 1970.
Neuberger, Nature Biotechnology 14:826, 1996.
Pearson & Lipman, *Proc. Nat'l. Acad. Sci. USA* 85:2444, 1988.
Pickar, Dosage Calculations, 1999.
Presta, Curr. Op. Struct. Biol. 2:593-596, 1992.
Riechmann et al., Nature 332:323-327, 1988.
Rizo & Gierasch, Ann. Rev. Biochem., 61:387, 1992.
Roguska et al., Prot. Engin., 9:895-904, 1996.
Saldanha et al., Mol. Immunol. 36:709-19, 1999.
Sambrook et al., Molecular Cloning. A Laboratory Manual (2d ed., Cold Spring Harbor Laboratory Press, N.Y., 1989 and 2001.
Sidman et al., Biopolymers, 22:547-556, 1983.
Sippl et al., Structure, 4(1):15-19, 1996.
Smith, D. W., ed., Biocomputing Informatics and Genome Projects, New York: Academic Press, 1993.
Smith et al., J. Virol., 46: 584, 1983.
Smith & Waterman, Adv. Appl. Math. 2:482, 1981.
Songsivilai et al., Clin. Exp. Immunol., 79:315-321, 1990.
Stahli et al., Methods in Enzymology 9:242-253, 1983.
Suresh et al., Methods in Enzymology 121:210, 1986.
Thornton et al., Nature, 354:105, 1991.
Thorpe "Antibody Carriers Of Cytotoxic Agents In Cancer Therapy: A Review" in Monoclonal Antibodies '84: Biological And Clinical Applications, Pinchera et al. (eds.), pp. 475-506, 1985.
Thorpe et al., "The Preparation and Cytotoxic Properties of Antibody-Toxin Conjugates", Immunol. Rev., 62:119-58, 1982.
Tijssen, Techniques in Biochemistry and Molecular Biology—Hybridization with Nucleic Probes, "Overview of principles of hybridization and the strategy of nucleic acid assays", 1993.
Traunecker et al., EMBO J. 10:3655-3659, 1991.
Vaswami et al., Annals of Allergy, Asthma, & Immunol. 81:105, 1998.
Veber & Freidinger, TINS, p. 392, 1985.
Verhocyen et al., Science 239:1534-1536, 1988.
von Heinje, G, Sequence Analysis in Molecular Biology, New York: Academic Press; Sequence Analysis Primer., 1987.
Wakankar et al., Biochemistry, Feb. 46(5) 1534-1544, Jan. 2007.
Winter, FEBS Letts., 430:92-94, 1998.

* cited by examiner

Vectibix D92 Isomerization Detected by LYS-C Peptide Map, pH 5.8 at 37°C for 6 Months Structural Model of Light Chain D92, IsoD92, E92 and N92 Variants

FIG. 4

Potency of Vectibix Mutants in Cell Based Assays

Bioassay - Potency

| Sample | Phosphorylation %Potency | Gene Express %Potency |
|---|---|---|
| Wild Type | 99 (4*) | 105 (6) |
| D → E | 115 (3) | 102 (6) |
| D → N | 90 (4) | 79 (6) |

*Number of measurements

ANTIGEN BINDING PROTEINS

This application is based on, and claims the benefit of, U.S. Provisional Application Ser. No. 61/473,014, filed Apr. 7, 2011 which is expressly incorporated herein by reference in its entirety.

REFERENCE TO THE SEQUENCE LISTING

The present application is being filed along with a Sequence Listing in electronic format. The Sequence Listing is provided as a file entitled A-1628-US-NP_SeqList.txt, created Apr. 6, 2012, which is 14 KB in size. The information in the electronic format of the Sequence Listing is incorporated herein by reference in its entirety.

BACKGROUND OF THE INVENTION

Epidermal Growth Factor Receptor (also termed "EGFR", "ErbB receptor", or "ErbB1 receptor") is a receptor protein tyrosine kinase which belongs to the ErbB receptor family. The ErbB receptor family includes ErbB (also known as ErbB1, or Her-1 receptor), ErbB2 (Her-2 receptor), ErbB3 (Her-3 receptor) and ErbB4 (Her-4 receptor), and other members of this family. Accordingly, the terms "ErbB1", "ErbB1 receptor," "ErbB receptor," "epidermal growth factor receptor," and "EGFR" are used interchangeably herein and refer to EGFR as disclosed, for example, in Carpenter et al. *Ann. Rev. Biochem.* 56:881-914 (1987), including naturally occurring mutant forms thereof (e.g., a deletion mutant EGFR as in Humphrey et al. *PNAS (USA)* 87:4207-4211 (1990)). It will be appreciated that as used herein, "EGFR" may be a native sequence EGFR or an amino acid sequence variant thereof.

EGFR generally comprises an extracellular domain, which may bind an ErbB ligand (such as EGF, TGF-α, etc.); a lipophilic transmembrane domain; a conserved intracellular tyrosine kinase domain; and a carboxyl-terminal signaling domain harboring several tyrosine residues which can be phosphorylated.

EGFR and its ligand, Epidermal Growth Factor ("EGF") have been implicated in cellular proliferation and many types of cancers, including, human solid tumors. See e.g., Mendelsohn, *Cancer Cell,* 7:359 (1989); Mendelsohn, *Cancer Biology* 1:339-344 (1990), Modjtahedi and Dean Int'l, *J. Oncology* 4:277-296 (1994). This includes lung cancer, breast cancer, colorectal cancers, gastric cancer, brain cancer, cancer of the bladder, head and neck cancers, ovarian cancer, and prostate carcinomas. Modjtahedi and Dean, *Intl J. Oncology* 4:277-296 (1994).

A number of anti-EGFR antibodies are available commercially, or are currently in clinical development. Such antibodies include, but are not limited to, Vectibix® (panitumumab), Erbitux® (cetuximab); zalatumumab, nimotuzumab, and matuzumab.

Panitumumab (sold under the trade name Vectibix®), is a human, anti-EGFR monoclonal antibody approved for certain treatments of metastatic colorectal cancer (mCRC) in the U.S., Europe, Japan, and a number of other countries around the world. The nucleic and amino acid sequences for panitumumab are known, and can be found, inter alia, in U.S. Pat. Nos. 6,235,883 and 7,807,798 (Jakobovits et al.). The contents of these patents are hereby incorporated by reference in their entirety. The heavy chain (gamma) sequence of panitumumab is set forth in Seq Id No. 1, herein. The light chain (kappa) sequence of panitumumab is set forth in Seq Id No. 2, herein. As used herein, the term "AMG 954" refers to Vectibix® (panitumumab).

Isomerization of certain amino acid residues is an observed phenomenon in antibodies. For example, Wakankar et al. observed that certain aspartic acid residues (Asp) in the light chain Complementarity Determining Regions (CDRs) of two recombinant monoclonal antibodies were susceptible to such isomerization. Specifically, aspartic acid (Asp) isomerization in these antibodies led to formation of isoaspartate (IsoAsp), and the cyclic imide (Asu) variants of these antibodies. See Wakankar et al., *Biochemistry,* 2007 Feb. 13; 46(6):1534-44 (January 2007). The formation of these variants was found to reduce the binding affinities of these antibodies, thereby reducing their potency. Id.

Isomerization of certain amino acids has been observed with respect to Vectibix® (panitumumab). This isomerization appears to relate to certain losses in potency, as well as the possibility of chemical degradation, and is thus undesirable. There thus exists a strong desire to eliminate or reduce this isomerization.

As will be seen, the mutants described herein have (i) retained potency, or (ii) improved stability, or (iii) both.

SUMMARY OF THE INVENTION

It has now been unexpectedly found that certain point mutations in panitumumab can alleviate the undesired isomerization and the resultant degradation in panitumumab. For example panitumumab mutants have light chain amino acids changed from D92 to N92, and D92 to E92 have demonstrated a retained potency and/or improved stability over panitumumab.

Accelerated stability studies at pH 5.8 and 5.0, at 37° C., have shown that the light chain (LC) CDR3 aspartic acid residue D92 of panitumumab is prone to isomerization, resulting in loss of activity. To evaluate whether it would be possible to eliminate this issue by modifying the primary sequence, two mutants were made, with a single point-mutation in each mutant: D92 to N92 (the "N" mutant); and D92 to E92 (the "E" mutant) in CDR3 of the light chain (LC). Both mutants retained biological activity measured by cell based potency assays. In addition, a stability study indicated that the D92 to E92 mutant was significantly more stable than Vectibix® (panitumumab) under accelerated conditions while retaining potency. The D92 to N92 mutant similarly retained potency, albeit without an observed improvement in stability.

The invention thus relates to antigen binding proteins, or fragments thereof, such as those found in Seq Id No. 3, and/or Seq Id No. 4, Seq Id No. 5, and/or Seq Id. No. 6. The antigen binding proteins of the invention can be monoclonal antibodies, or fragment thereof, and include, but are not limited to human antibodies, humanized antibodies, chimeric antibodies, multispecific antibodies, and fragments thereof.

In other aspects, the invention relates to an antigen binding protein comprising the region spanning CDRs 1-3 of Seq Id No. 3. The invention further relates to an antigen binding protein comprising the region spanning CDRs 1-3 of Seq Id No. 4.

The invention also relates to an anti-EGFR antibody having a point mutation at position 92, wherein said point mutation is a glutamic acid residue or an asparagine.

The invention further relates to a method for improving the stability of an EGFR antibody, such as panitumumab, comprising changing the aspartic acid residue at position 92 to a glutamic acid residue or an asparagine residue.

Further, the invention relates to isolated antigen binding proteins described herein capable of reducing binding (or other interaction) of EGFR to EGF and/or TGF-α. The invention also relates to an isolated antigen binding protein that competes for binding to EGFR with an antigen binding protein described herein.

The invention also relates to a nucleic acid molecule encoding the antigen binding protein, or portion thereof, as set forth in any of Seq Id Nos. 3, 4, 5, or 6. The nucleic acid molecule can be operably linked to a control sequence. In other aspects, the invention relates to a vector comprising this/these nucleic acid molecules, and further to hosts cells comprising these vectors.

The invention further relates to a method of making an antigen binding protein described herein comprising the step of preparing said antigen binding protein from a host cell that secretes said antigen binding protein.

In other aspects, the invention relates to a pharmaceutical composition comprising at least one antigen binding protein (such as an antibody) described herein and a pharmaceutically acceptable excipient.

The invention also relates to pharmaceutical compositions comprising one or more antigen binding protein described herein, further comprising a radioisotope, a radionuclide, a toxin, a therapeutic agent, or a chemotherapeutic agent.

In still other aspects, the invention relates to methods for treating or preventing cancer comprising administering to a patient in thereof an effective amount of at least one isolated antigen binding protein as described herein. The invention further relates to methods for treating or preventing a condition associated with at least one of elevated EGF and EGFR levels in a patient, comprising administering to a patient in thereof an effective amount of at least one isolated antigen binding protein as described herein. The invention also relates to methods of inhibiting binding of EGFR to EGF in a patient, comprising administering an effective amount of at least one antigen binding protein as described herein.

In some aspects, the invention comprises an isolated antigen binding protein that binds EGFR comprising one or more light chain complementary determining regions (CDRs) set forth in Seq Id No. 3 and/or Seq Id No. 4.

For clarity, it will be appreciated that the CDRs in the antigen binding proteins are underlined, and set forth in consecutive order, i.e., CDR1, CDR2, CDR3.

In some aspects, the invention comprises an isolated antigen binding protein that specifically binds to an epitope that is bound by any of the antigen binding proteins disclosed herein.

Other aspects of the invention will be appreciated by one skilled in the art, and are described herein.

BRIEF DESCRIPTIONS OF THE FIGURES

FIG. 1 shows Vectibix® (panitumumab) D92 isomerization as detected by Lys-C peptide map, pH 5.8 at 37° C. for 6 months. Vectibix® (panitumumab) was incubated in formulation buffer at pH 5.8 for 6 months at 37° C. The samples were compared to the reference standard using Lys-C peptide mapping. The level of isomerization was quantified by the ratio of modified and original peptide Lys-L3 (residues 46-103). "A" represents the hybridoma-derived molecule, and "B" shows the CHO-derived molecule.

Figure 2:
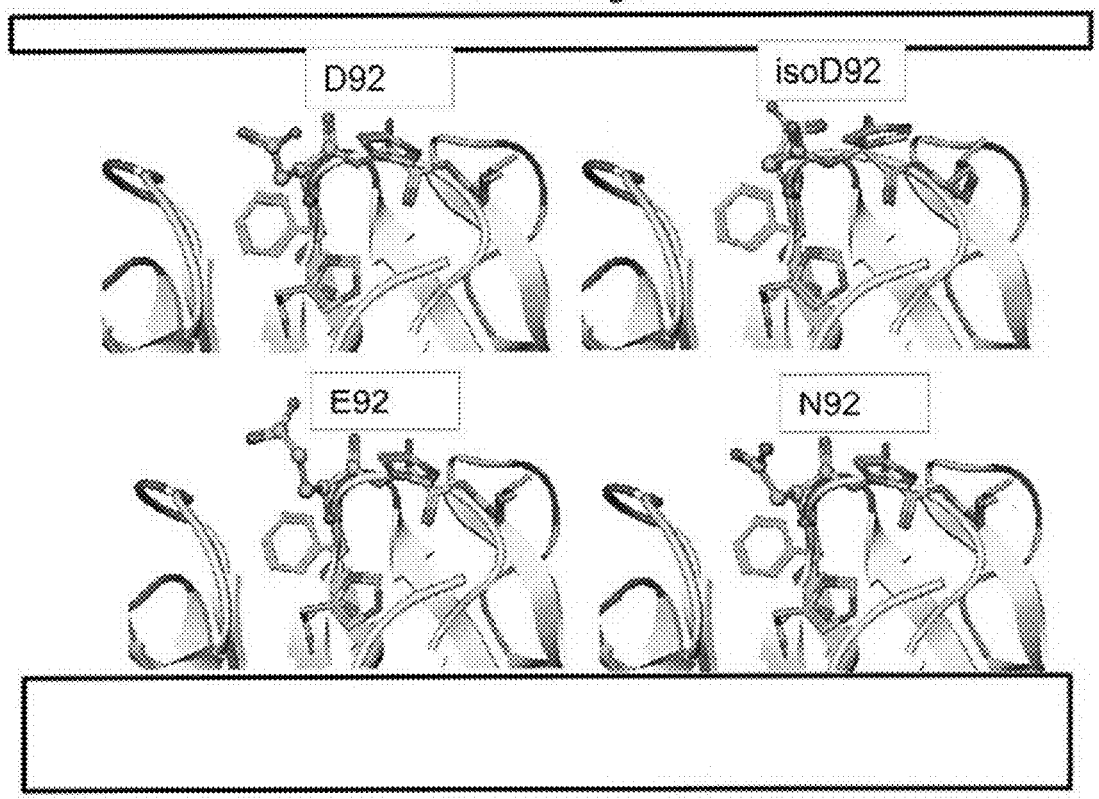

FIG. 2 shows a structural model of light chain (LC) D92, isoD92, E92 and N92.

Figure 3:
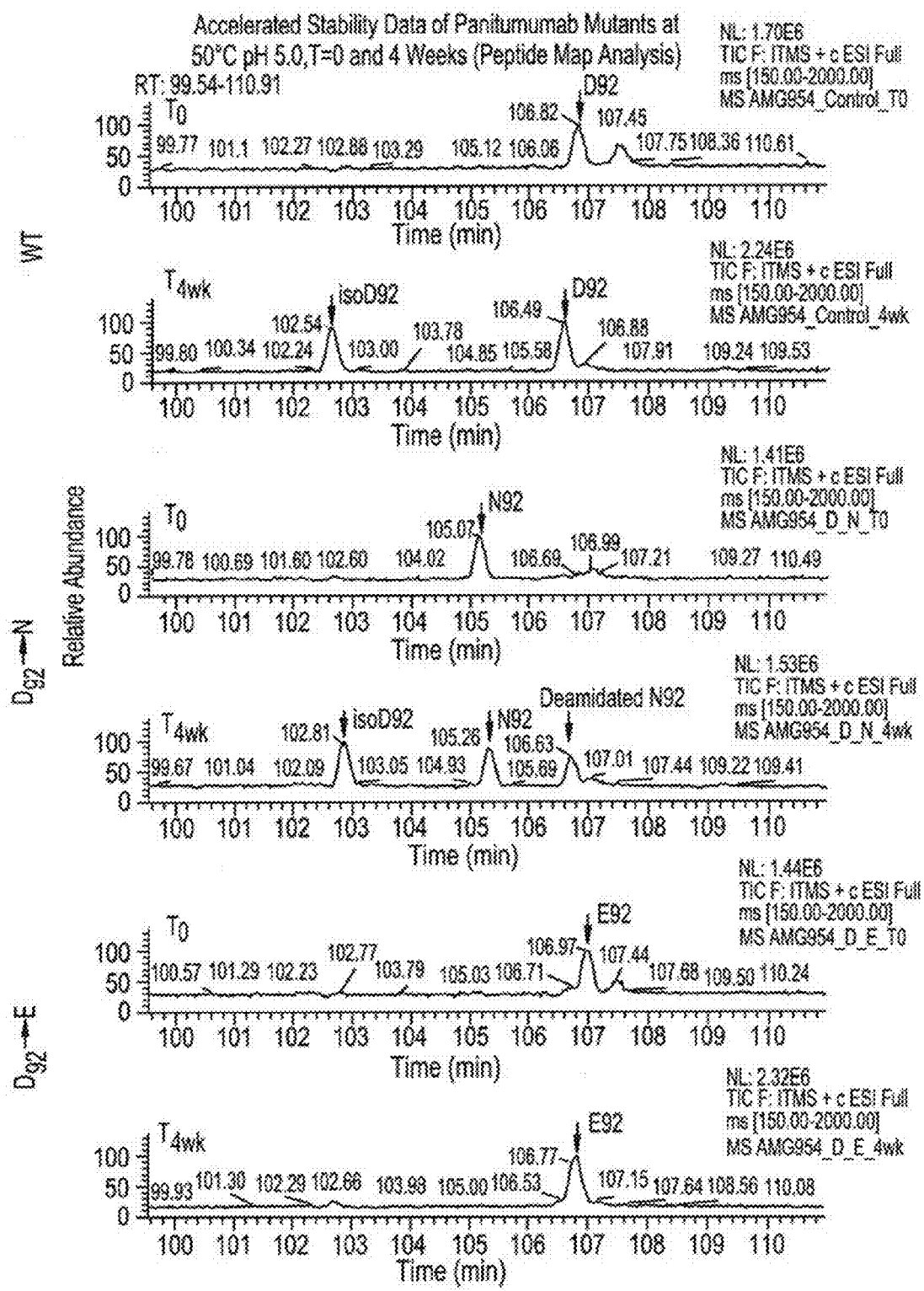

FIG. 3 shows accelerated stability data of Vectibix® (panitumumab) mutants, pH 5.0 at 50° C. for 4 weeks. Wild-type Vectibix® (D92) and the two mutants (E92, N92) were incubated at pH 5.0 for 4 weeks at 50° C. Comparison of the stressed samples to the untreated material by tryptic mapping showed that peptide Trp-L5 was distributed as follows: wild type molecule two Trp-L5 peaks (D92 and isoD92), mutant N92 three Trp-L5 peaks (N92, D92 and isoD92), and mutant E92 one Trp-L5 peak (E92). This result shows, inter alia, that mutant E92 is stable under these accelerated stress conditions.

FIG. 4 shows the potency of the Vectibix® (panitumumab) mutants in cell-based assays.

DETAILED DESCRIPTION

Antigen binding proteins (such as antibodies and functional binding fragments thereof) that bind to EGFR are disclosed herein. In some embodiments, the antigen binding proteins bind to EGFR and prevent EGFR from functioning in various ways. In some embodiments, the antigen binding proteins block or reduce the ability of EGFR to interact with other substances. For example, in some embodiments, the antigen binding protein binds to EGFR in a manner that prevents or reduces the likelihood that EGFR will bind to EGF. In other embodiments, antigen binding proteins bind to EGFR but may not block EGFR's ability to interact with EGF. In some embodiments, the antigen binding proteins are human monoclonal antibodies.

Antigen binding proteins to EGFR can be used in the treatment and/or prevention of various cancers, including but not limited to colorectal, breast, lung, head and neck, ovarian, cervical, prostate, pancreatic, and the like. Accordingly, methods and compositions for treating subjects with cancer are within the scope of the present invention, as described herein.

For convenience, the following sections generally outline the various meanings of the terms used herein. Following this discussion, general aspects regarding antigen binding proteins are discussed, followed by specific examples demonstrating the properties of various embodiments of the antigen binding proteins and how they can be employed.

Definitions and Embodiments

It will be understood that the descriptions herein are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

The term "EGFR" refers to the Epidermal Growth Factor Receptor, fragments thereof, as well as related polypeptides, which include, but are not limited to, allelic variants, splice variants, derivative variants, substitution variants, deletion variants, and/or insertion variants including the addition of an N-terminal methionine, fusion polypeptides, and interspecies homologs. In certain embodiments, an EGFR polypeptide includes terminal residues, such as, but not limited to, signal peptide sequence residues, targeting residues, amino terminal methionine residues, lysine residues, tag residues and/or fusion protein residues. Reference to EGFR includes variants, isoforms and species homologs of human EGFR. In a preferred embodiment, binding of an antibody of the invention to the EGFR-antigen inhibits the growth of cells expressing EGFR (e.g., a tumor cell) by inhibiting or blocking binding of one or more EGFR ligand/s to EGFR. The term "EGFR ligand" encompasses all (e.g., physiological) ligands for EGFR, including but not limited to EGF, TGF-αlpha, heparin binding EGF (HB-EGF), amphiregulin (AR), heregulin, betacellulin, and epiregulin (EPI). In another preferred embodiment, binding of an antibody of the invention to the EGFR-antigen mediates effector cell phagocytosis and/or killing of cells expressing EGFR.

The extracellular part of the mature EGFR (SwissProt acc.#P00533) consists of 621 amino acids and four receptor domains: Domain I encompasses residues 1-165, domain II residues 166-312, domain III residues 313-481 and domain IV 482-621 (Cochran et al. (2004) *J. Immunol. Methods*, 287, 147-158). Domains I and III have been suggested to contribute to the formation of high affinity binding sites for ligands. Domains II and IV are cysteine rich, laminin-like regions that stabilize protein folding and contain a possible EGFR dimerization interface.

Biomarkers

Certain mutations in the KRAS gene have been found to be predictive of non-responsiveness to an EGFR inhibitor, such as an antibody. See e.g., US 2008/0293055, "KRAS mutations and Anti-EGFR Antibody Therapy" to Freeman et al., the contents of which are hereby incorporated by reference in their entirety. A number of such KRAS mutations have been identified, including but not limited to: G12S, G12V, G12D, G12A, G12C, G13A, G13D, and T20M.

Additional biomarkers, including NRAS, PTEN, and PIP3, are described in Asghar et al., *Clin. Colorectal Cancer.*, December, 9(5):274-81 (2010). Another potential biomarker, EGFR gene copy number, is described in US 2007/0087394 and US 2009/0269344, the contents of which are hereby incorporated by reference in their entirety.

The terms "mutant EGFR polynucleotide," "mutant EGFR oligonucleotide," and "mutant EGFR nucleic acid" are used interchangeably, and refer to a polynucleotide encoding an EGFR polypeptide comprising at least one EGFR mutation selected from L688P, Q701H, K745N, C781R, a histidine insertion between amino acids 771 and 772, T790M, L828stop, Q849R, F910L, and V948A. See e.g., US 2007/0048754, to Freeman et al., hereby incorporated by reference.

The terms "mutant P13K polynucleotide," "mutant P13K oligonucleotide," and "mutant P13K nucleic acid" are used interchangeably, and refer to a polynucleotide encoding a P13K polypeptide comprising at least one P13K mutation selected from E542K, E545A, and H1047L.

The terms "mutant B-Raf polynucleotide," "mutant B-Raf oligonucleotide," and "mutant B-Raf nucleic acid" are used interchangeably, and refer to a polynucleotide encoding a B-Raf polypeptide with at least one B-Raf mutation. These mutations are described in US 2009/0075267, the contents of which are hereby incorporated by reference in their entirety.

As used herein, the term "cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostrate, penis, testicle, vulva, vagina, cervical and ovary tissues.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more in comparison to a normal cell or comparison cell (e.g., a BPH cell).

The terms "cancer-associated antigen" or "tumor-specific marker" or "tumor marker" interchangeably refers to a molecule (typically protein, carbohydrate or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is expressed or stabilized with minimal degradation in a cancer cell in comparison to a normal cell, for instance, 2-fold expression, 3-fold expression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell. Also, a cancer-associated antigen can be expressed exclusively in a cancer cell and not synthesized or expressed in a normal cell. Exemplified cell surface tumor markers include the proteins c-erbB-2 and human epidermal growth factor receptor (EGFR) for breast cancer, PSMA for prostate cancer, and carbohydrate mucins in numerous cancers, including breast, ovarian and colorectal.

An "agonist" refers to an agent that binds to a polypeptide or polynucleotide (such as a receptor) of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

Cytotoxic agents include "cell-cycle specific" or "antimitotic" or "cytoskeletal-interacting" drugs. These terms interchangeably refer to any pharmacological agent that blocks cells in mitosis. Such agents are useful in chemotherapy. Generally, cell-cycle-specific-drugs bind to the cytoskeletal protein tubulin and block the ability of tubulin to polymerize into microtubules, resulting in the arrest of cell division at metaphase. Exemplified cell-cycle-specific drugs include vinca alkaloids, taxanes, colchicine, and podophyllotoxin. Exemplified vinca alkaloids include vinblastine, vincristine, vindesine and vinorelbine. Exemplified taxanes include paclitaxel and docetaxel. Another example of a cytoskeletal-interacting drug includes 2-methoxyestradiol.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length, e.g., each complementary sequence of the double stranded siRNA is 15-50 nucleotides in length, and the double stranded siRNA is about 15-50 base pairs in length, preferably about 20-30 base nucleotides, preferably about 20-25 or about 24-29 nucleotides in length, e.g., 20, 21, 22, 23, 24, 25, 26, 27, 28, 29, or 30 nucleotides in length.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or through manual alignment and also visual inspection (see e.g., the NCBI website http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described herein, the preferred algorithms can account for gaps, and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto. The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass EGFR antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a EGFR-binding antibody, useful fragments include but are not limited to a CDR region, a variable domain of a heavy and/or light chain, a portion of an antibody chain or just its variable region including two CDRs, and the like.

The term "isolated protein" referred means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or non-covalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

The term "amino acid" refers to natural and non-naturally occurring amino acids, and includes its normal meaning in the art.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are typically aligned in a way that gives the largest match between the sequences. One example of a computer program that can be used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Examples of parameters that can be employed in determining percent identity for polypeptides or nucleotide sequences using the GAP program are the following:

Algorithm: Needleman et al., 1970, *J. Mol. Biol.* 48:443-453

Comparison matrix: BLOSUM 62 from Henikoff et al., 1992, supra

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, the twenty conventional (e.g., naturally occurring) amino acids and their abbreviations follow conventional usage. See *Immunology—A Synthesis* (2nd Ed., E. S. Golub & D. R. Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:
  Hydrophobic: Norleucine, Met, Ala, Val, Leu, Ile;
  Neutral hydrophilic: Cys, Ser, Thr, Asn, Gln;
  Acidic: Asp, Glu;
  Basic: H is, Lys, Arg;
  Residues that influence chain orientation: Gly, Pro; and
  Aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the antigen binding protein (such as an antibody), according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5) and tryptophan (-3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by at least one linkage selected from: —$CH_2NH$—, —$CH_2S$—, —$CH_2$—$CH_2$—, —CH=CH— (cis & trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo & Gierasch, Ann. Rev. Biochem., 61:387 (1992), incorporated herein by reference for any purpose); for example, by adding internal cysteine residues capable of forming intramolecular disulfide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

An "antigen binding protein" ("ABP") as used herein means any protein that binds a specified target antigen. In the instant application, the specified target antigen is the EGFR protein or fragment or region thereof "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In some embodiments, the fragments can block or reduce the likelihood of the interaction between EGF and EGFR. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding protein comprises or consists of avimers (tightly binding peptide). These various antigen binding proteins are further described herein.

An "Fc" region comprises two heavy chain fragments comprising the $C_H1$ and $C_H2$ domains of an antibody. The two heavy chain fragments are held together by two or more disulfide bonds and by hydrophobic interactions of the $C_H3$ domains.

A "Fab fragment" comprises one light chain and the $C_H1$ and variable regions of one heavy chain. The heavy chain of a Fab molecule cannot form a disulfide bond with another heavy chain molecule.

A "Fab' fragment" comprises one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific as defined herein. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific," or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which can reside on the same or different protein targets.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$, $C_H2$ and $C_H3$. The antibodies that are provided can have any of these isotypes and subtypes. In certain embodiments of the present invention, an anti-EGFR antibody is of the IgG2 or IgG4 subtype.

An antigen binding protein is said to "specifically bind" its target antigen when the dissociation constant ($K_d$) is $\leq 10^{-7}$ M. The antigen binding protein specifically binds antigen with "high affinity" when the $K_d$ is $\leq 5 \times 10^{-9}$ M, and with "very high affinity" when the $K_d$ is $\leq 5 \times 10^{-10}$ M. In one embodiment, the antigen binding protein has a $K_d$ of $\leq 10^{-9}$ M. In one embodiment, the off-rate is $< 1 \times 10^{-5}$. In other embodiments, the antigen binding proteins will bind to human EGFR with a $K_d$ of between about $10^{-9}$ M and $10^{-13}$ M, and in yet another embodiment the antigen binding proteins will bind with a $K_d \leq 5 \times 10^{-10}$. As will be appreciated by one of skill in the art, in some embodiments, any or all of the antigen binding fragments can specifically bind to EGFR.

An antigen binding protein is "selective" when it binds to one target more tightly than it binds to a second target.

"Antigen binding region" means a protein, or a portion of a protein, that specifically binds a specified antigen (e.g., a paratope). For example, that portion of an antigen binding protein that contains the amino acid residues that interact with an antigen and confer on the antigen binding protein its specificity and affinity for the antigen is referred to as "antigen binding region." An antigen binding region typically includes one or more Complementary Binding Regions (CDRs). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen. Structurally, framework regions can be located in antibodies between CDRs.

In certain aspects, recombinant antigen binding proteins that bind EGFR, for example human EGFR, are provided. In this context, a "recombinant antigen binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See e.g., *Fundamental Immunology*, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, *J. Mol. Biol.*, 196:901-917 (1987); Chothia et al., *Nature,* 342:878-883 (1989).

It will be appreciated that the "92" numbering used herein refers amino acid number 92. It will be appreciated that amino acid number 92 is in this case the same position whether using Kabat numbering, or simply counting directly following the signal peptide sequence for the panitumumab antibody mutants.

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the "AbM" definition and the contact definition.

The Kabat definition is a standard for numbering the residues in an antibody and is typically used to identify CDR regions. See e.g., Johnson & Wu, *Nucleic Acids Res.,* 28:214-8 (2000). The Chothia definition is similar to the Kabat definition, but the Chothia definition takes into account positions of certain structural loop regions. See e.g., Chothia et al., *J. Mol. Biol.,* 196: 901-17 (1986); Chothia et al., *Nature,* 342: 877-83 (1989). The "AbM" definition uses an integrated suite of computer programs produced by Oxford Molecular Group that model antibody structure. See e.g., Martin et al., *Proc. Natl. Acad. Sci.* (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See e.g., MacCallum et al., *J. Mol. Biol.,* 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

Specificity of the present antibodies, or fragments thereof, for EGFR can be determined based on affinity and/or avidity. Affinity, represented by the equilibrium constant for the dissociation of an antigen with an antibody (Kd), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites specific for a particular epitope. Antibodies typically bind with a dissociation constant (Kd) of $10^{-5}$ to $10^{-11}$ liters/mol. Any Kd greater than $10^{-4}$ liters/mol is generally considered to indicate nonspecific binding. The lesser the value of the Kd, the stronger the binding strength between an antigenic determinant and the antibody binding site.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See e.g., Songsivilai et al., *Clin. Exp. Immunol.,* 79:315-321 (1990); Kostelny et al., *J. Immunol.,* 148:1547-1553 (1992).

Some species of mammals also produce antibodies having only a single heavy chain.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains;

the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$, $C_H2$ and $C_H3$. The antibodies that are provided can have any of these isotypes and subtypes. In certain embodiments of the present invention, an anti-EGFR antibody is of the IgG2 or IgG4 subtype.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target The term "neutralizing antigen binding protein" or "neutralizing antibody" refers to an antigen binding protein or antibody, respectively, that binds to a ligand and prevents or reduces the binding of the ligand to a binding partner. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In some embodiments, in the case of EGFR antigen binding proteins, such a neutralizing molecule can diminish the ability of EGFR to bind the EGF. In some embodiments, the neutralizing ability is characterized and/or described via a competition assay. In some embodiments, the neutralizing ability is described in terms of an $IC_{50}$ or $EC_{50}$ value. In some embodiments, the antigen binding proteins may be non-neutralizing antigen binding proteins.

The term "target" refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., EGFR or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see e.g., Stahli et al., 1983, *Methods in Enzymology* 9:242-253); solid phase direct biotin-avidin EIA (see e.g., Kirkland et al., 1986, *J. Immunol.* 137:3614-3619) solid phase direct labeled assay, solid phase direct labeled sandwich assay (see e.g., Harlow and Lane, 1988, *Antibodies, A Laboratory Manual*, Cold Spring Harbor Press); solid phase direct label RIA using I-125 label (see e.g., Morel et al., 1988, *Molec. Immunol.* 25:7-15); solid phase direct biotin-avidin EIA (see e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen" refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen binding proteins, e.g., antibodies.

The term "epitope" includes any determinant capable being bound by an antigen binding protein, such as an antibody or to a T-cell receptor. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, $\beta$-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The terms "therapeutically effective amount" and "therapeutically effective dose" refer to the amount of a EGFR antigen binding protein determined to produce a therapeutic response in a mammal. Such therapeutically effective amounts are readily ascertained by one of ordinary skill in the art. The exact dose and formulation will depend on the purpose of the treatment, and will be ascertainable by one skilled in the art using known techniques (see e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule.

Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen binding proteins (ABPs) that bind EGFR, including human EGFR, are provided herein. In some embodiments, the antigen binding proteins provided are polypeptides which comprise one or more complementary determining regions (CDRs), as described herein. In some antigen binding proteins, the CDRs are embedded into a "framework" region, which orients the CDR(s) such that the proper antigen binding properties of the CDR(s) is achieved. In some embodiments, antigen binding proteins provided herein can interfere with, block, reduce or modulate the interaction between EGFR and EGF. Such antigen binding proteins are denoted as "neutralizing." In some embodiments, the neutralizing antigen binding protein binds to EGFR in a location and/or manner that prevents EGFR from binding to EGF.

In some embodiments, the antigen binding proteins provided herein are capable of inhibiting EGFR-mediated activity (including binding). In some embodiments, antigen binding proteins binding to these epitopes inhibit, inter alia, interactions between EGFR and EGF and other physiological effects mediated by EGFR. In some embodiments, the antigen binding proteins are human, such as fully human antibodies to EGFR.

In some embodiments, the antigen binding protein binds to the catalytic domain of EGFR. In some embodiments, the antigen binding protein binds to the mature form of EGFR. In some embodiments the antigen binding protein binds in the prodomain of EGFR. In some embodiments, the antigen binding protein selectively binds to the mature form of EGFR. In some embodiments, the antigen binding protein binds to the catalytic domain in a manner such that EGFR cannot bind or bind as efficiently to EGF. In some embodiments, the antigen binding protein does not bind to the c-terminus of the catalytic domain. In some embodiments, the antigen binding protein does not bind to the n-terminus of the catalytic domain. In some embodiments, the antigen binding protein does not bind to the N- or C-terminus of the EGFR protein. In some embodiments, the antigen binding protein binds to any one of the epitopes bound by the antibodies discussed herein. In some embodiments, this can be determined by competition assays between the antibodies disclosed herein and other antibodies. In some embodiments, the antigen binding protein binds to an epitope bound by one of the antibodies described herein. In some embodiments, the antigen binding proteins bind to a specific conformational state of EGFR so as to prevent EGFR from interacting with EGF.

The antigen binding proteins that are disclosed herein have a variety of utilities. Some of the antigen binding proteins, for instance, are useful in specific binding assays, affinity purification of EGFR, in particular human EGFR or its ligands and in screening assays to identify other antagonists of EGFR activity. Some of the antigen binding proteins are useful for inhibiting binding of EGFR to EGF, or inhibiting EGFR-mediated activities.

The antigen binding proteins can be used in a variety of therapeutic applications, as explained herein. For example, in some embodiments the EGFR antigen binding proteins are useful for treating diseases and conditions associated with EGF and/or EGFR, such as cancer, as further described herein.

In some embodiments, the antigen binding proteins that are provided comprise one or more CDRs (e.g., 1, 2, 3, 4, 5 or 6 CDRs). In some embodiments, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab fragment, a Fab' fragment, a F(ab')$_2$ fragment, an Fv fragment, a diabody, or a single chain antibody molecule, such as an scFv)

In embodiments where the antigen binding protein is used for therapeutic applications, an antigen binding protein can inhibit, interfere with or modulate one or more biological activities of EGFR. In one embodiment, an antigen binding protein binds specifically to human EGFR and/or substantially inhibits binding of human EGFR to EGF by at least about 20%-40%, 40-60%, 60-80%, 80-85%, or more (for example, by measuring binding in an in vitro competitive binding assay). Some of the antigen binding proteins that are provided herein are antibodies. In some embodiments, the antigen binding protein has a $K_d$ of less (binding more tightly) than $10^{-7}$, $10^{-8}$, $10^{-9}$, $10^{-10}$, $10^{-11}$, $10^{-12}$, $10^{-13}$ M. In some embodiments, the antigen binding protein has an $IC_{50}$ for blocking the binding of EGF to EGFR of less than 1 μM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In some embodiments, the antigen binding proteins bind to a specific conformational state of EGFR so as to prevent EGFR from interacting with EGF.

Humanized Antigen Binding Proteins (e.g., Antibodies)

As described herein, an antigen binding protein to EGFR can comprise a humanized antibody and/or part thereof. An important practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See e.g., U.S. Pat. Nos. 5,530,101, 5,693,761; 5,693,762; and 5,585,089.

In certain embodiments, amino acids of an antibody variable domain that can be modified without diminishing the native affinity of the antigen binding domain while reducing its immunogenicity are identified. See e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See e.g., Co et al., Mol. Immunol., 30:1361-1367 (1993). In certain embodiments, techniques such as "reshaping," "hyperchimerization," or "veneering/resurfacing" are used to produce humanized antibodies. See e.g., Vaswami et al., *Annals of Allergy, Asthma, & Immunol.* 81:105 (1998); Roguska et al., *Prot. Engin.*, 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., *J. Immunol.*, 62(6):3663-71 (1999).

In certain instances, humanizing antibodies results in a loss of antigen binding capacity. In certain embodiments, humanized antibodies are "back mutated." In certain such embodiments, the humanized antibody is mutated to include one or more of the amino acid residues found in the donor antibody. See e.g., Saldanha et al., *Mol. Immunol.* 36:709-19 (1999).

In certain embodiments the complementarity determining regions (CDRs) of the light and heavy chain variable regions of an antibody to EGFR can be grafted to framework regions (FRs) from the same, or another, species. In certain embodiments, the CDRs of the light and heavy chain variable regions of an antibody to EGFR can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to EGFR heavy chain or light chain are replaced with the FRs from a different heavy chain or light chain. In certain embodiments, rare amino acids in the FRs of the heavy and light chains of an antibody to EGFR are not replaced, while the rest of the FR amino acids are replaced. Rare amino acids are specific amino acids that are in positions in which they are not usually found in FRs. In certain embodiments, the grafted variable regions from an antibody to EGFR can be used with a constant region that is different from the constant region of an antibody to EGFR. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., Nature, 321: 522-525 (1986); Riechmann et al., Nature, 332: 323-327 (1988); Verhoeyen et al., Science, 239:1534-1536 (1988), Winter, FEBS Letts., 430:92-94 (1998), which are hereby incorporated by reference for any purpose.

Human Antigen Binding Proteins (e.g., Antibodies)

As described herein, an antigen binding protein that binds to EGFR can comprise a human (i.e., fully human) antibody and/or part thereof. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments, a purified human monoclonal antibody to human EGFR is provided.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in WO 98/24893, U.S. Pat. No. 5,545,807, EP 546073, and EP 546073.

In certain embodiments, one can use constant regions from species other than human along with the human variable region(s).

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

Humanized antibodies are those antibodies that, while initially starting off containing antibody amino acid sequences that are not human, have had at least some of these nonhuman antibody amino acid sequences replaced with human antibody sequences. This is in contrast with human antibodies, in which the antibody is encoded (or capable of being encoded) by genes possessed a human.

Antigen Binding Protein Variants

Other antibodies that are provided are variants of the antigen binding proteins listed above formed by combination or subparts of the variable heavy and variable light chains described herein and comprise variable light and/or variable heavy chains that each have at least 50%, 50-60, 60-70, 70-80%, 80-85%, 85-90%, 90-95%, 95-97%, 97-99%, or above 99% identity to the amino acid sequences of these sequences (either the entire sequence or a subpart of the sequence, e.g., one or more CDR). In some instances, such antibodies include at least one heavy chain and one light chain, whereas in other instances the variant forms contain two identical light chains and two identical heavy chains (or subparts thereof).

In certain embodiments, the antigen binding protein comprises an amino acid sequence at least 90% identical to an amino acid sequence set forth in Seq Id No: 3, Seq Id No. 4, Seq Id No. 5, or Seq Id No. 6. In certain embodiments, the antigen binding protein comprises an amino acid sequence at least 95% identical to an amino acid sequence set forth in Seq Id No: 3, Seq Id No. 4, Seq Id No. 5, or Seq Id No. 6. In certain embodiments, the antigen binding protein comprises an amino acid sequence at least 99% identical to an amino acid sequence set forth in Seq Id No: 3, Seq Id No. 4, Seq Id No. 5, or Seq Id No. 6.

In some embodiments, the antigen binding protein comprises a sequence that is at least 90%, 90-95%, and/or 95-99% identical to one or more CDRs recited in Seq Id No: 3, Seq Id No. 4, Seq Id No. 5, or Seq Id No. 6.

In light of the present disclosure, a skilled artisan will be able to determine suitable variants of the antigen binding proteins as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar antigen binding proteins. In view of such information, one skilled in the art can predict the alignment of amino acid residues of an antibody with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested in Brenner et al., *Curr. Op. Struct. Biol.*, 7(3):369-376 (1997) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3):377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci. USA*, 84(13):4355-4358 (1987)), and "evolutionary linkage" (See Holm, supra (1999), and Brenner, supra (1997)).

In certain embodiments, antigen binding protein variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden & J. Tooze, eds., Garland Publishing, New York, N.Y. (1991)); and Thornton et al., *Nature*, 354:105 (1991), which are each incorporated herein by reference.

In some embodiments, the variants are variants of the nucleic acid sequences of the antigen binding proteins disclosed herein. One of skill in the art will appreciate that the above discussion can be used for identifying, evaluating, and/or creating antigen binding protein variants and also for nucleic acid sequences that can encode for those protein variants.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 seconds-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

Preparation of Antigen Binding Proteins (e.g., Antibodies)

In certain embodiments, antigen binding proteins (such as antibodies) are produced by immunization with an antigen (e.g., EGFR). In certain embodiments, antibodies can be produced by immunization with full-length EGFR, a soluble form of EGFR, the catalytic domain alone, the mature form of EGFR, a splice variant form of EGFR, or a fragment thereof. In certain embodiments, the antibodies of the invention can be polyclonal or monoclonal, and/or can be recombinant antibodies. In certain embodiments, antibodies of the invention are human antibodies prepared, for example, by immunization of transgenic animals capable of producing human antibodies (see e.g., PCT Published Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See e.g., Hudson, Curr. Opin. Biotech., 9:395-402 (1999) and references therein.

In certain embodiments, smaller and more effectively screened libraries of antibody variants are produced by restricting random or site-directed mutagenesis to hyper-mutation sites in the CDRs, which are sites that correspond to areas prone to mutation during the somatic affinity maturation process. See e.g., Chowdhury & Pastan, Nature Biotech., 17: 568-572 (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetra-base sequence comprising a purine (A or G), followed by guanine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

Preparation of Fully Human Antigen Binding Proteins (e.g., Antibodies)

In certain embodiments, a phage display technique is used to generate monoclonal antibodies. In certain embodiments, such techniques produce fully human monoclonal antibodies. In certain embodiments, a polynucleotide encoding a single Fab or Fv antibody fragment is expressed on the surface of a phage particle. See e.g., Hoogenboom et al., J. Mol. Biol., 227: 381 (1991); Marks et al., J Mol. Biol. 222: 581 (1991); U.S. Pat. No. 5,885,793. In certain embodiments, phage are "screened" to identify those antibody fragments having affinity for target. Thus, certain such processes mimic immune selection through the display of antibody fragment repertoires on the surface of filamentous bacteriophage, and subsequent selection of phage by their binding to target. In certain such procedures, high affinity functional neutralizing antibody fragments are isolated. In certain such embodiments (discussed in more detail below), a complete repertoire of human antibody genes is created by cloning naturally rearranged human V genes from peripheral blood lymphocytes. See e.g., Mullinax et al., Proc Natl Acad Sci (USA), 87: 8095-8099 (1990).

According to certain embodiments, antibodies of the invention are prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving this result are disclosed in the patents, applications and references disclosed in the specification, herein. In certain embodiments, one can employ methods such as those disclosed in PCT Published Application No. WO 98/24893 or in Mendez et al., Nature Genetics, 15:146-156 (1997), which are hereby incorporated by reference for any purpose.

Generally, fully human monoclonal antigen binding proteins (e.g., antibodies) specific for EGFR can be produced as follows. Transgenic mice containing human immunoglobulin genes are immunized with the antigen of interest, e.g. EGFR, lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to EGFR is provided.

In certain embodiments, fully human antibodies are produced by exposing human splenocytes (B or T cells) to an antigen in vitro, and then reconstituting the exposed cells in an immunocompromised mouse, e.g. SCID or nod/SCID. See e.g., Brams et al., J. Immunol. 160: 2051-2058 (1998); Carballido et al., Nat. Med., 6: 103-106 (2000). In certain such approaches, engraftment of human fetal tissue into SCID mice (SCID-hu) results in long-term hematopoiesis and human T-cell development. See e.g., McCune et al., *Science*, 241:1532-1639 (1988); Ifversen et al., *Sem. Immunol.*, 8:243-248 (1996). In certain instances, humoral immune response in such chimeric mice is dependent on co-development of human T-cells in the animals. See e.g., Martensson et al., *Immunol.*, 83:1271-179 (1994). In certain approaches, human peripheral blood lymphocytes are transplanted into SCID mice. See e.g., Mosier et al., *Nature*, 335:256-259 (1988). In certain such embodiments, when such transplanted cells are treated either with a priming agent, such as Staphylococcal Enterotoxin A (SEA), or with anti-human CD40 monoclonal antibodies, higher levels of B cell production is detected. See e.g., Martensson et al., *Immunol.*, 84: 224-230 (1995); Murphy et al., *Blood*, 86:1946-1953 (1995).

Thus, in certain embodiments, fully human antibodies can be produced by the expression of recombinant DNA in host cells or by expression in hybridoma cells. In other embodiments, antibodies can be produced using the phage display techniques described herein.

The antibodies described herein were prepared in part through the utilization of the XenoMouse® technology, as described herein. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., *Nature Genetics*, 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. EGFR), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to EGFR Further, provided herein are characterization of the antibodies produced by such cell lines, including nucleotide and amino acid sequence analyses of the heavy and light chains of such antibodies.

The production of the XenoMouse® strains of mice is further discussed and delineated in U.S. patent application Ser. Nos. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000.

The development of fully human monoclonal antibody (Mab) technology has become an important milestone towards fulfilling the promise of antibody therapy in human disease. Human monoclonal antibodies minimize immunogenic and allergic responses intrinsic to murine or humanized antibodies, and have demonstrated increased efficacy and/or safety. A number of techniques exist for producing human monoclonal antibodies, including, but not limited to the XenoMouse® approach pioneered by Abgenix (now part of Amgen Inc.). See Green et al., *Nature Genetics* 7:13-21 (1994). Further variations of Xenomouse® technology can be found in Mendez et al., *Nature Genetics* 15:146-156 (1997) and U.S. patent application Ser. No. 08/759,620, the disclosures of which are hereby incorporated by reference in their entirety.

In an alternative approach, others, including GenPharm International Inc., have used a "minilocus" approach to producing human antibodies. This approach is described in U.S. Pat. No. 5,545,807 to Surani et al. and U.S. Pat. Nos. 5,545,806 and 5,625,825, both to Lonberg and Kay, and U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209, 741, filed Mar. 9, 1994, the disclosures of which are hereby incorporated by reference. See also WO 94/25585, WO 93/12227, WO 92/22645, and WO 92/03918, the disclosures of which are hereby incorporated by reference in their entirety. Additional techniques for producing human antibodies have been developed by, e.g., Medarex® (now part of Bristol Myers Squibb®), and Cambridge Antibody Technologies® (CAT, now part of AstraZeneca®).

The disclosures of each of the above-cited patents, applications, and references are also hereby incorporated by reference in their entirety.

For preparation of suitable antibodies of the invention and for use according to the invention, e.g., recombinant, monoclonal, or polyclonal antibodies, many techniques known in the art can be used (see e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see e.g., Kuby, *Immunol.* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see e.g., U.S. Pat. Nos. 5,545,807; 5,545,806; 5,569,825; 5,625,126; 5,633,425; 5,661,016; Marks et al., *Bio/Technology,* 10:779-783 (1992); Lonberg et al., *Nature,* 368:856-859 (1994); Morrison, *Nature,* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see e.g., McCafferty et al., *Nature* 348:552-554 (1990); Marks et al., *Biotechnology* 10:779-783 (1992)). Antibodies can also be made bispecific, i.e., able to recognize two different antigens (see e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg & Kay, U.S. Pat. Nos. 5,591,669 and 6,023.010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. Nos. 07/574,748, 07/575,962, 07/810,279, 07/853,408, 07/904, 068, 07/990,860, 08/053,131, 08/096,762, 08/155,301, 08/161,739, 08/165,699, 08/209,741, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773288 and 843961, the disclosures of which are hereby incorporated by reference. Additionally, KM™ mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

In some embodiments, the antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-13}$ M or below, when measured by various techniques.

In one embodiment, the antibody is conjugated to an "effector" moiety. The effector moiety can be any number of molecules, including labeling moieties such as radioactive labels or fluorescent labels, or can be a therapeutic moiety.

The antibodies of this invention can be fused to additional amino acid residues. Such amino acid residues can be a peptide tag, perhaps to facilitate isolation. Other amino acid residues for homing of the antibodies to specific organs or tissues are also contemplated.

In another aspect of the invention, anti-EGFR antibodies or antibody fragments can be chemically or biosynthetically linked to anti-tumor agents or detectable signal-producing agents. As exemplified below, antibodies of the invention are efficiently internalized upon binding to cells bearing EGFR. Anti-tumor agents linked to an antibody include any agents which destroy or damage a tumor to which the antibody has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods (See, e.g., Hermentin and Seiler, *Behring Inst. Mitt.* 82:197-215 (1988)).

Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible region, and can be substrates or degradation products of enzyme catalyzed reactions.

In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a N-cadherin positive cell, particularly cells, which express the N-cadherin or Ly6 protein. Such differences can be readily apparent when viewing the bands of gels with approximately similarly loaded with test and controls samples. Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally. In some embodiments, the patient has a urogenital cancer (e.g., bladder cancer, prostate cancer). In some embodiments of the above, the patient suffers from prostate cancer and optionally further receives patient hormone ablation therapy. In some embodiments, the contacting comprises administering the antibody directly into the cancer or a metastasis of the cancer. In some embodiments, the chemotherapeutic agent can be selected from the group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin.

Additionally, the recombinant protein of the invention comprising the antigen-binding region of any of the monoclonal antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, ricin, abrin, glucocorticoid and radioisotopes.

Techniques for conjugating therapeutic agents to antibodies are well known (see e.g., Arnon et al., "Monoclonal Antibodies For Immunotargeting Of Drugs In Cancer Therapy", in Monoclonal Antibodies & Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive EGFR binding properties.

In certain embodiments, the antigen binding proteins (such as antibodies) bind to EGFR with a dissociation constant ($K_D$) of less than approximately 1 nM, e.g., 1000 pM to 100 pM, 100 pM to 10 pM, 10 pM to 1 pM, and/or 1 pM to 0.1 pM or less.

In certain embodiments, antigen binding proteins comprise an immunoglobulin molecule of at least one of the IgG1, IgG2, IgG3, IgG4, Ig E, IgA, IgD, and IgM isotype. In certain embodiments, antigen binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen binding proteins have been cloned for expression in mammalian cells. In certain embodiments, antigen binding proteins comprise a constant region other than any of the constant regions of the IgG1, IgG2, IgG3, IgG4, IgE, IgA, IgD, and IgM isotype.

In certain embodiments, antigen binding proteins comprise a human lambda light chain and a human IgG2 heavy chain. In certain embodiments, antigen binding proteins comprise a human lambda light chain and a human IgG4 heavy chain. In certain embodiments, antigen binding proteins comprise a human lambda light chain and a human IgG1, IgG3, IgE, IgA, IgD or IgM heavy chain. In other embodiments, antigen binding proteins comprise a human kappa light chain and a human IgG2 heavy chain. In certain embodiments, antigen binding proteins comprise a human kappa light chain and a human IgG4 heavy chain. In certain embodiments, antigen binding proteins comprise a human kappa light chain and a human IgG1, IgG3, IgE, IgA, IgD or IgM heavy chain. In certain embodiments, antigen binding proteins comprise variable regions of antibodies ligated to a constant region that is neither the constant region for the IgG2 isotype, nor the constant region for the IgG4 isotype. In certain embodiments, antigen binding proteins have been cloned for expression in mammalian cells.

In contrast, in certain embodiments, substantial modifications in the functional and/or chemical characteristics of antibodies to EGFR can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to EGFR, or to increase or decrease the affinity of the antibodies to EGFR as described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen binding proteins comprise one or more polypeptides. In certain embodiments, any of a variety of expression vector/host systems can be utilized to express polynucleotide molecules encoding polypeptides comprising one or more antigen binding protein components or the antigen binding protein itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more antigen binding protein components or the antigen binding protein itself is recombinantly expressed in yeast. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more antigen binding protein components or the antigen binding protein itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more antigen binding protein components or the antigen binding protein itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more antigen binding protein components or the antigen binding protein itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia* larvae. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia* larvae. See e.g., Smith et al., *J. Virol.*, 46: 584 (1983); Engelhard et al., *Proc. Nat. Acad. Sci.* (USA), 91: 3224-7 (1994).

In certain embodiments, polypeptides comprising one or more antigen binding protein components or the antigen binding protein itself made in bacterial cells are produced as insoluble inclusion bodies in the bacteria. In certain embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (see e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more antigen binding protein components or the antigen binding protein itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more antigen binding protein components or the antigen binding protein itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromatography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more antigen binding protein components or the antigen binding protein itself is partially purified. In certain embodiments, partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See e.g., Capaldi et al., *Biochem. Biophys. Res. Comm.*, 76: 425 (1977). It will be appreciated that under different electrophoresis conditions, the apparent molecular weights of purified or partially purified polypeptide can be different.

Exemplary Epitopes

Epitopes to which anti-EGFR antibodies bind have been described. Freeman et al., *Journal of Clinical Oncol.*, 26:14536 (2008); ASCO Annual Meeting Proceedings. In some embodiments, antigen binding proteins that bind to EGFR epitopes, or that competitively bind to the EGFR antibody epitopes are useful.

Certain Therapeutic Uses and Pharmaceutical Compositions

In some embodiments, more than one antigen binding protein to EGFR is used to modulate EGFR activity.

In certain embodiments, an antigen binding protein to EGFR is administered alone. In certain embodiments, an antigen binding protein to EGFR is administered prior to the administration of at least one other therapeutic agent. In certain embodiments, an antigen binding protein to EGFR is administered concurrent with the administration of at least one other therapeutic agent. In certain embodiments, an antigen binding protein to EGFR is administered subsequent to the administration of at least one other therapeutic agent. In other embodiments, an antigen binding protein to EGFR is administered prior to the administration of at least one other therapeutic agent.

In an embodiment of the invention, anti-EGFR antibodies can be administered in combination with one or more other anti-neoplastic agents. For examples of combination therapies, see e.g., U.S. Pat. No. 6,217,866 (Schlessinger et al.) (Anti-EGFR antibodies in combination with anti-neoplastic agents); WO 99/60023 (Waksal et al.) (Anti-EGFR antibodies in combination with radiation). Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine, and topoisomerase inhibitors irinotecan (CPT-11), aminocamptothecin, camptothecin, DX-8951f, and topotecan (topoisomerase I) and etoposide (VP-16) and teniposide (VM-26) (topoisomerase II). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

The anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents.

Among these classes, the data reported herein suggest that topoisomerase inhibitors are particularly effective anti-neoplastic agents when used in combination with antibodies that bind to EGFR. Accordingly, embodiments of the invention include methods in which a topoisomerase inhibitor is administered in combination with an antibody that binds to EGFR. The inhibitors can be inhibitors of topoisomerase I or topoisomerase II. Topoisomerase I inhibitors include irinotecan (CPT-11), amino-camptothecin, camptothecin, DX-8951f, topotecan. Topoisomerase II inhibitors include etoposide (VP-16), and teniposide (VM-26). Other substances are currently being evaluated with respect to topoisomerase inhibitory activity and effectiveness as anti-neoplastic agents. In a preferred embodiment, the topoisomerase inhibitor is irinotecan (CPT-11). The antibodies used in combination are antibodies of the invention that bind to EGFR and have at least one of the following properties: (i) inhibit binding of EGF to EGFR; (ii) neutralize activation of EGFR by EGF (iii) reduce EGFR surface receptor; and bind to EGFR with a Kd of about $1 \times 10^{-10}$ $M^{-1}$ or less. In a more preferred embodiment, the antibodies to be used in combination with a topoisomerase inhibitor have the characteristics of the human antibodies set forth above.

Anti-EGFR antibodies of the invention can be administered with antibodies that neutralize other receptors involved in tumor growth or angiogenesis. In an embodiment of the invention, an anti-EGFR antibody is used in combination with a receptor antagonist that binds specifically to EGFR. Particularly preferred are antigen-binding proteins that bind to the extracellular domain of EGFR and block binding of one or more of its ligands and/or neutralize ligand-induced activation of EGFR. An EGFR antagonist can be an antibody that binds to EGFR or a ligand of EGFR and inhibits binding of EGFR to its ligand. Ligands for EGFR include, for example, EGF, TGF-α, amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. It should be appreciated that the EGFR antagonist can bind externally to the extracellular portion of EGFR, which can or cannot inhibit binding of the ligand, or internally to the tyrosine kinase domain. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Another example of such a receptor is VEGFR. In an embodiment of the present invention, an anti-EGFR antibody is used in combination with a VEGFR antagonist. In one embodiment of the invention, an anti-EGFR antibody is used in combination with a receptor antagonist that binds specifically to VEGFR-1/Flt-1 receptor. In another embodiment, an anti-EGFR antibody is used in combination with a receptor antagonist that binds specifically to VEGFR-2/KDR receptor. Particularly preferred are antigen-binding proteins that bind to the extracellular domain of VEGFR-1 or VEGFR-2 and block binding by their ligands (VEGFR-2 is stimulated most strongly by VEGF; VEGFR-1 is stimulated most strongly by P1GF, but also by VEGF) and/or neutralize ligand-induced induced activation. For example, IMC-1121 is a human antibody that binds to and neutralizes VEGFR-2 (WO 03/075840; Zhu). Another example is MAb 6.12 is a scFv that binds to soluble and cell surface-expressed VEGFR-1. ScFv 6.12 comprises the $V_L$ and $V_H$ domains of mouse monoclonal antibody MAb 6.12. A hybridoma cell line producing MAb 6.12 has been deposited as ATCC number PTA-3344 under the provisions of the Budapest Treaty on the International Recognition of the Deposit of Microorganisms for the Purposes of Patent Procedure and the regulations thereunder (Budapest Treaty). Other examples of growth factor receptors involved in tumorigenesis are the receptors for platelet-derived growth factor (PDGFR), nerve growth factor (NGFR), and fibroblast growth factor (FGFR).

In an additional alternative embodiment, the EGFR antibody can be administered in combination with one or more suitable adjuvants, such as, for example, cytokines (IL-10 and IL-13, for example) or other immune stimulators, such as, but not limited to, chemokine, tumor-associated antigens, and peptides. See, e.g., Larrivée et al., supra. It should be appreciated, however, that administration of only an anti-EGFR antibody is sufficient to prevent, inhibit, or reduce the progression of the tumor in a therapeutically effective manner.

In a combination therapy, the anti-EGFR antibody is administered before, during, or after commencing therapy with another agent, as well as any combination thereof, i.e., before and during, before and after, during and after, or before, during and after commencing the anti-neoplastic agent therapy.

For example, the anti-EGFR antibody can be administered between 1 and 30 days, preferably 3 and 20 days, more preferably between 5 and 12 days before commencing radiation therapy. In a preferred embodiment of the invention, chemotherapy is administered concurrently with or, more preferably, subsequent to antibody therapy. In another aspect of the invention, an anti-EGFR antibody of the invention can be chemically or biosynthetically linked to one or more anti-neoplastic or anti-angiogenic agents.

The invention further contemplates anti-EGFR antibodies to which target or reporter moieties are linked. Target moieties are first members of binding pairs. Anti-neoplastic agents, for example, are conjugated to second members of such pairs and are thereby directed to the site where the anti-EGFR antibody is bound. A common example of such a binding pair is avidin and biotin. In a preferred embodiment, biotin is conjugated to an anti-EGFR antibody, and thereby provides a target for an anti-neoplastic agent or other moiety, which is conjugated to avidin or streptavidin. Alternatively, biotin or another such moiety is linked to an anti-EGFR antibody of the invention and used as a reporter, for example in a diagnostic system where a detectable signal-producing agent is conjugated to avidin or streptavidin.

It is understood that the anti-EGFR antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The present invention also includes kits for inhibiting tumor growth and/or angiogenesis comprising a therapeutically effective amount of a human anti-EGFR antibody. The kits can further contain any suitable antagonist of, for example, another growth factor receptor involved in tumorigenesis or angiogenesis (e.g., EGFR, VEGFR-1/Flt-1, VEGFR-2, PDGFR, NGFR, FGFR, etc, as described above). Alternatively, or in addition, the kits of the present invention can further comprise an anti-neoplastic agent. Examples of suitable anti-neoplastic agents in the context of the present invention have been described herein. The kits of the present invention can further comprise an adjuvant; examples have also been described above.

Moreover, included within the scope of the present invention is use of the present antibodies in vivo and in vitro for investigative or diagnostic methods, which are well known in the art. The diagnostic methods include kits, which contain antibodies of the present invention.

Accordingly, the present receptor antibodies thus can be used in vivo and in vitro for investigative, diagnostic, prophylactic, or treatment methods, which are well known in the art. Of course, it is to be understood and expected that variations in the principles of invention herein disclosed can be made by one skilled in the art and it is intended that such modifications are to be included within the scope of the present invention.

A method of treating tumor growth in a mammal by administering to the mammal an effective amount of an antibody as previously described is also provided by the present invention. The EGFR signaling pathway has been extensively demonstrated to be a causative factor in the development of many types of cancer.

In the present invention, any suitable method or route can be used to administer anti-EGFR antibodies of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity tumor being treated and the route of administration of the antagonists. It should be emphasized, however, that the present invention is not limited to any particular method or route of administration.

It is noted that an anti-EGFR antibody of the invention can be administered as a conjugate, which binds specifically to the receptor and delivers a toxic, lethal payload following ligand-toxin internalization. The antibody-drug/small molecule conjugate can be directly linked to each other or via a linker, peptide or non-peptide.

In certain embodiments, an antigen binding protein to EGFR is used with particular therapeutic agents to treat various cancers. In certain embodiments, in view of the condition and the desired level of treatment, two, three, or more agents can be administered. In certain embodiments, such agents can be provided together by inclusion in the same formulation. In certain embodiments, such agents can be formulated separately and provided together by inclusion in a treatment kit. In certain embodiments, such agents and an antigen binding protein to EGFR can be formulated separately and provided together by inclusion in a treatment kit. In certain embodiments, such agents can be provided separately. In certain embodiments, when administered by gene therapy, the genes encoding protein agents and/or an antigen binding protein to EGFR can be included in the same vector. In certain embodiments, the genes encoding protein agents and/or an antigen binding protein to EGFR can be under the control of the same promoter region. In certain embodiments, the genes encoding protein agents and/or an antigen binding protein to EGFR can be in separate vectors.

In certain embodiments, the invention provides for pharmaceutical compositions comprising an antigen binding protein to EGFR together with a pharmaceutically acceptable diluent, carrier, solubilizer, emulsifier, preservative and/or adjuvant.

In certain embodiments, an antigen binding protein to EGFR can be used with at least one therapeutic agent for inflammation. In certain embodiments, an antigen binding protein to EGFR can be used with at least one therapeutic agent for an immune disorder. Exemplary therapeutic agents for inflammation and immune disorders include, but are not limited to cyclooxygenase type-1 (COX-1) and cyclooxygenase type-2 (COX-2) inhibitors small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and lck. Certain exemplary therapeutic agents for inflammation are described, e.g., in C. A. Dinarello & L. L. Moldawer *Proinflammatory and Anti-Inflammatory Cytokines in Rheumatoid Arthritis: A Primer for Clinicians,* 3rd Edition (2001) Amgen Inc., Thousand Oaks, Calif.

In certain embodiments, pharmaceutical compositions will include more than one different antigen binding protein to EGFR. In certain embodiments, pharmaceutical compositions will include more than one antigen binding protein to EGFR wherein the antigen binding proteins to EGFR bind more than one epitope. In some embodiments, the various antigen binding proteins will not compete with one another for binding to EGFR. In some embodiments, any of the antigen binding proteins described herein can be combined together in a pharmaceutical composition.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapol); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Ed., A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, an antigen binding protein to EGFR and/or a therapeutic molecule is linked to a half-life extending vehicle known in the art. Such vehicles include, but are not limited to, polyethylene glycol, glycogen (e.g., glycosylation of the antigen binding protein), and dextran. Such vehicles are described, e.g., in U.S. application Ser. No. 09/428,082, now U.S. Pat. No. 6,660,843 and published PCT Application No. WO 99/25044, hereby incorporated by reference.

In certain embodiments, the optimal pharmaceutical composition will be determined by one skilled in the art depending upon, for example, the intended route of administration, delivery format and desired dosage. See e.g., *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antigen binding protein to EGFR, with or without at least one additional therapeutic agents, can be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising an antigen binding protein to EGFR, with or without at least one additional therapeutic agents, can be formulated as a lyophilizate using appropriate excipients such as sucrose.

Pharmaceutical formulations, particularly, of the antibodies and immuno-conjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g., Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunoconjugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as SFU, vinblastine, actinomycin D, cisplatin, methotrexate, and the like.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired antigen binding protein to EGFR, with or without additional therapeutic agents, in a pharmaceutically acceptable vehicle. In certain embodiments, a vehicle for parenteral injection is sterile distilled water in which an antigen binding protein to EGFR, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an antigen binding protein to EGFR, with or without at least one additional therapeutic agent, can be formulated as a dry powder for inhalation. In certain embodiments, an inhalation solution comprising an antigen binding protein to EGFR, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, an antigen binding protein to EGFR, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an antigen binding protein to EGFR and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an antigen binding protein to EGFR, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antigen binding proteins to EGFR, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., *Biopolymers*, 22:547-556 (1983)), poly (2-hydroxyethyl-methacrylate) (Langer et al., *J. Biomed. Mater. Res.*, 15:167-277 (1981) and Langer, Chem. Tech., 12:98-105 (1982)), ethylene vinyl acetate (Langer et al., supra) or poly-D(-)-3-hydroxybutyric acid (EP 133,988). In certain embodiments, sustained release compositions can also include liposomes, which can be prepared by any of several methods known in the art. See e.g., Eppstein et al., *Proc. Natl. Acad. Sci. USA*, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an antigen binding protein to EGFR, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an antigen binding protein to EGFR, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1

μg/kg to up to about 100 mg/kg or more, depending on the factors mentioned above. In certain embodiments, the dosage can range from 0.1 μg/kg up to about 100 mg/kg; or 1 μg/kg up to about 100 mg/kg; or 5 μg/kg up to about 100 mg/kg.

In certain embodiments, the frequency of dosing will take into account the pharmacokinetic parameters of an antigen binding protein to EGFR and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising an antigen binding protein to EGFR, with or without at least one additional therapeutic agent, in an ex vivo manner. In such instances, cells, tissues and/or organs that have been removed from the patient are exposed to a pharmaceutical composition comprising an antigen binding protein to EGFR, with or without at least one additional therapeutic agent, after which the cells, tissues and/or organs are subsequently implanted back into the patient.

In certain embodiments, an antigen binding protein to EGFR and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein products) but prevent the destruction of the cells by the patient's immune system or by other detrimental factors from the surrounding tissues.

Diagnostic Applications

In some embodiments, the antigen binding proteins disclosed herein are used or provided in an assay kit and/or method for the detection of EGFR in mammalian tissues or cells in order to screen/diagnose for a disease or disorder associated with changes in levels of EGFR. The kit comprises an antigen binding protein that binds EGFR and means for indicating the binding of the antigen binding protein with EGFR, if present, and optionally EGFR protein levels. Various means for indicating the presence of an antigen binding protein can be used. For example, fluorophores, other molecular probes, or enzymes can be linked to the antigen binding protein and the presence of the antigen binding protein can be observed in a variety of ways. The method for screening for such disorders can involve the use of the kit, or simply the use of one of the disclosed antigen binding proteins and the determination of whether the antigen binding protein binds to EGFR in a sample. As will be appreciated by one of skill in the art, high or elevated levels of EGFR will result in larger amounts of the antigen binding protein binding to EGFR in the sample. Thus, degree of antigen binding protein binding can be used to determine how much EGFR is in a sample. Subjects or samples with an amount of EGFR that is greater than a predetermined amount (e.g., an amount or range that a person without a EGFR related disorder would have) can be characterized as having an EGF and/or EGFR mediated disorder.

The relevant amino acid and nucleic acid sequences of panitumumab, and the respective mutants are set forth in Table 2.

TABLE 2

| | | | |
|---|---|---|---|
| Seq Id No. 1 | QVQLQESGPG | LVKPSETLSL | TCTVSGGSVS |
| Panitumumab heavy chain | SGDYYWTWIR | QSPGKGLEWI | 50 |
| (gamma) amino acid | GHIYYSGNTN | YNPSLKSRLT | ISIDTSKTQF |
| sequence, (including Fc | SLKLSSVTAA | DTAIYYCVRD | 100 |
| Portion) | RVTGAFDIWG | QGTMVTVSSA | STKGPSVFPL |
| | APCSRSTSES | TAALGCLVKD | 150 |
| | YFPEPVTVSW | NSGALTSGVH | TFPAVLQSSG |
| | LYSLSSVVTV | PSSNFGTQTY | 200 |
| | TCNVDHKPSN | TKVDKTVERK | CCVECPPCPA-(hinge) |
| | PPVAGPSVFL | FPPKPKDTLM | 250 |
| | ISRTPEVTCV | VVDVSHEDPE | VQFNWYVDGV |
| | EVHNAKTKPR | EEQFNSTFRV | 300 |
| | VSVLTVVHQD | WLNGKEYKCK | VSNKGLPAPI |
| | EKTISKTKGQ | PREPQVYTLP | 350 |
| | PSREEMTKNQ | VSLTCLVKGF | YPSDIAVEWE |
| | SNGQPENNYK | TTPPMLDSDG | 400 |
| | SFFLYSKLTV | DKSRWQQGNV | FSCSVMHEAL |
| | HNHYTQKSLS | LSPGK 445 | |

TABLE 2-continued

| | |
|---|---|
| Seq Id No. 2<br>Panitumumab light chain<br>(kappa) amino acid<br>sequence | DIQMTQSPSS LSASVGDRVT ITC QASQDISNYLN<br>WYQQKP GKAPKLLIYD 50<br>ASNLETGVPS RFSGSGSGTD FTFTISSLQP<br>EDIATYFCQHFDHLPLAFGG 100<br>GTKVEIKRTV AAPSVFIFPP SDEQLKSGTA<br>SVVCLLNNFY PREAKVQWKV 150<br>DNALQSGNSQ ESVTEQDSKD STYSLSSTLT<br>LSKADYEKHK VYACEVTHQG 200<br>LSSPVTKSFN RGEC 214 |
| Seq Id No. 3<br>Panitumumab light chain<br>(kappa) amino acid<br>sequence with "E"<br>mutation | DIQMTQSPSS LSASVGDRVT ITC QASQDISNYLN<br>WYQQKP GKAPKLLIYD 50<br>ASNLETGVPS RFSGSGSGTD FTFTISSLQP<br>EDIATYFC QHFEHLPLAFGG 100<br>GTKVEIKRTV AAPSVFIFPP SDEQLKSGTA<br>SVVCLLNNFY PREAKVQWKV 150<br>DNALQSGNSQ ESVTEQDSKD STYSLSSTLT<br>LSKADYEKHK VYACEVTHQG 200<br>LSSPVTKSFN RGEC 214 |
| Seq Id No. 4<br>Panitumumab Light Chain<br>(Kappa) amino acid<br>sequence with "N"<br>mutation | DIQMTQSPSS LSASVGDRVT ITC QASQDISNYLN<br>WYQQKP GKAPKLLIYD 50<br>ASNLETGVPS RFSGSGSGTD FTFTISSLQP<br>EDIATYFC QHFNHLPLAFGG 100<br>GTKVEIKRTV AAPSVFIFPP SDEQLKSGTA<br>SVVCLLNNFY PREAKVQWKV 150<br>DNALQSGNSQ ESVTEQDSKD STYSLSSTLT<br>LSKADYEKHK VYACEVTHQG 200<br>LSSPVTKSFN RGEC 214 |
| Seq Id No. 5<br>Light chain kappa variable<br>region CDR 3 amino acid<br>sequence with "E"<br>mutation | QHFEHLPLA |
| Seq Id No. 6<br>Light chain kappa variable<br>region CDR 3 amino acid<br>sequence with "N"<br>mutation | QHFNHLPLA |
| Seq Id No 7<br>Light chain (kappa) nucleic<br>acid sequence with "92E"<br>mutation | atgagggtccctgctcagctcctggggctcctgctgctctggctctcaggtgccag<br>atgtgacatccagatgacccagtctccatcctccctgtctgcatctgtaggagacag<br>agtcaccatcacttgccaggcgagtcaggacatcagcaactatttaaattggtatca<br>gcagaaaccagggaaagcccctaaactcctgatctacgatgcatccaatttggaaa<br>cagggggtcccatcaaggttcagtggaagtggatctgggacagattttactttcacca<br>tcagcagcctgcagcctgaagatattgcaacatatttctgtcaacactttgagcatct<br>cccgctcgctttcggcggagggaccaaggtggagatcaaacgaactgtggctgc<br>accatctgtcttcatcttcccgccatctgatgagcagttgaaatctggaactgcctctg<br>ttgtgtgcctgctgaataacttctatcccagagaggccaaagtacagtggaaggtg<br>gataacgcccctccaatcgggtaactcccaggagagtgtcacagagcaggacagc<br>aaggacagcacctacagcctcagcagcaccctgacgctgagcaaagcagactac<br>gagaaacacaaagtctacgcctgcgaagtcacccatcagggcctgagctcgccc<br>gtcacaaagagcttcaacaggggagagtgttag |
| Seq Id No. 8<br>Light chain (kappa) nucleic<br>acid sequence with "92N"<br>mutation | atgagggtccctgctcagctcctggggctcctgctgctctggctctcaggtgccag<br>atgtgacatccagatgacccagtctccatcctccctgtctgcatctgtaggagacag<br>agtcaccatcacttgccaggcgagtcaggacatcagcaactatttaaattggtatca<br>gcagaaaccagggaaagcccctaaactcctgatctacgatgcatccaatttggaaa<br>cagggggtcccatcaaggttcagtggaagtggatctgggacagattttactttcacca<br>tcagcagcctgcagcctgaagatattgcaacatatttctgtcaacactttaatcatctc<br>ccgctcgctttcggcggagggaccaaggtggagatcaaacgaactgtggctgca<br>ccatctgtcttcatcttcccgccatctgatgagcagttgaaatctggaactgcctctgt<br>tgtgtgcctgctgaataacttctatcccagagaggccaaagtacagtggaaggtgg<br>ataacgcccctccaatcgggtaactcccaggagagtgtcacagagcaggacagca<br>aggacagcacctacagcctcagcagcaccctgacgctgagcaaagcagactacg<br>agaaacacaaagtctacgcctgcgaagtcacccatcagggcctgagctcgcccgt<br>cacaaagagcttcaacaggggagagtgttag |
| Seq Id No. 9<br>Light chain kappa variable<br>region CDR3 nucleic acid<br>sequence with "E"<br>mutation | caacactttgagcatctcccgctcgct |

TABLE 2-continued

Seq Id No. 10
Light chain kappa variable
region CDR3 nucleic acid
sequence with "N"
mutation caacactttaatcatctcccgctcgct The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The following examples, including the experiments conducted and results achieved, are provided for illustrative purposes only and are not to be construed as limiting the present invention.

EXAMPLE 1

Mutagenesis

The heavy and light chain amino acid sequences for panitumumab (Seq Id Nos. 1 & 2) were used as a starting material for mutagenesis. PCR primers were designed to perform site directed mutagenesis using the Quik Change II XL® Site Directed Mutagenesis Kit from Stratagene (Now Agilent Technologies, Inc., Santa Clara, Calif.). Following the manufacturer's protocol, PCR reactions were set up using the oligonucleotides and used to transform XL-Gold ultra-competent cells. These cells were then plated onto TIM selective plates. The plates were placed at 37° C. overnight to allow for colony formation. Two colonies from each construct were picked and re-streaked on TIM plates. One colony of each construct was then set up for maxipreps. The maxipreps were sequenced and matched 100%. Sal I-Not I digests were performed on the maxipreps to select fragments of interest. The two restriction ends were ligated into Sal I-Not I digested pDC414. The new ligations were transformed into DH10B competent cells and plated out on TIM selection plates. The plates were then placed at 37° C. overnight to allow colony formation. Several colonies were digested to test for insertion. One maxiprep was made for each mutation: pDC414-AMG954 Asp92-Glu, and pDC414-AMG954 Asp92-Asn. The maxipreps were sequenced and matched 100%. Megapreps were transient transfected using 293(E) cells. The cells were cultured for 7 days and then harvested. The expressed antibodies were purified from the supernatant using a Protein A column and standard techniques.

Endoproteinases Lys-C and Trypsin Peptide Maps

The resultant molecule was then denatured and reduced, and the sulfhydryls were alkylated. The reduced-alkylated molecule was desalted by gel filtration and then enzymatically deglycosylated. The reduced-alkylated-deglycosylated molecule was then digested with Lys-C or Trypsin Endoproteinase. The reaction was quenched and the resulting fragments were separated by reversed phase HPLC in an acetonitrile/TFA gradient using for the Lys-C digest a polymer column (Grace-Vydac, Deerfield, Ill.), and for the tryptic digest a HPLC BEH Amide column (Waters, Milford, Mass.). Peptide elution was monitored by UV detection. Vectibix® (panitumumab) D92 isomerization results as detected by Lys-C peptide map is set forth in FIG. 1.

EXAMPLE 2

Structural Models

The structure of Vectibix® (panitumumab) was analyzed using the Molecular Operating Environment (MOE) software (Chemical Computing Group, Montreal, Canada). Isomerization was modeled by hand by breaking and forming the necessary atomic bonds within MOE. The specific mutations were modeled using the mutation capabilities built into the MOE modeling software. The results are set forth in FIG. 2.

EXAMPLE 3

Accelerated Stability Study

The stability study of Vectibix® (panitumumab) was performed at 37° C. for 6 months in 50 mM sodium acetate and 100 mM sodium chloride at pH 5.8. In order to accelerate isomerization, the mutants were buffer exchanged into 10 mM glutamic acid, 2.6% w/v Glycerol at pH 5.0 and subjected to elevated temperature at 50° C. for 4 weeks. The results are set forth in FIG. 3.

EXAMPLE 4

Bioassays

Phosphorylation Bioassay. The phosphorylation bioassay used was based upon the detection of EGF induced tyrosine phosphorylation of the EGF receptor. Vectibix® (panitumumab) binds to the EGF receptor, inhibiting EGF binding and hence receptor phosphorylation. A431 cells, which express cell surface EGF receptor, were incubated in microtiter plates with a fixed amount of EGF and a varying amounts of Vectibix®. The cells were lysed and soluble EGF receptor was captured on a second microtiter ELISA plate coated with an anti-EGF receptor antibody. Phosphorylated EGF receptors were detected by using an anti-phosphotyrosine antibody conjugated with HRP followed by addition of a chromogenic substrate. Color development was then measured using an absorbance plate reader. Relative potency was determined by parallel line analysis.

Gene Expression Bioassay. 32D MRE-1/S#13 cells were grown as a suspension culture in RPMI 1640 medium with Glutamax™ containing 10% FBS, 5 ng/mL mIL-3, 500 ug/mL G418, and 700 ug/mL hygromycin-B. Assay flasks of the cells were prepared for use by centrifugation and washing with phosphate buffered saline to eliminate growth medium components. The cells were then resuspended at 8E+05 cells/mL in assay medium (RPMI 1640 with Glutamax™ 1% FBS).

Reference standard, control, and test samples were diluted to 440 ng/mL in assay medium. Serial dilutions of reference standard, control, and test samples were prepared to yield a concentration range of 440 to 87 ng/mL. Following preparation of these dilutions, an equal volume of a fixed concentration of TGF-α was added to each tube. The final concentration in the assay wells was 110 to 22 ng/mL of Vectibix® after addition of cells.

The assay utilized four 96-well plates and a partially randomized sample location scheme. Twenty-five µL of each serial dilution of antibody mixed with TGF-α spike was added to assay wells. Twenty-five µL of assay medium was added to the cells only wells to serve as cell blanks. Fifty µL of assay medium was added to the media only wells to serve as media blanks. Twenty-five µL of TGF-α spike control was added to background wells (TGF-α spike control). All Standard, Control Sample, Test Sample, Background, and Cells Only wells then received 25 µL of 32D MRE-1/S #13 cell suspension at 8E+05 cells/mL. The plates were then incubated for 3.5±0.5 hours in a 37° C./5% $CO_2$ humidified incubator.

After the incubation period, the plates were removed from the incubator and cooled to room temperature for 10-20 minutes. Fifty µL of SteadyGlo® (a reagent cocktail containing a detergent to lyse the cells, and luciferin, a substrate for luciferase) was added to each well. The assay plates were then covered to minimize light exposure, and incubated at room temperature for 30-120 minutes. Luminescence signal was then quantitated using a luminometer. Test sample activity was determined by comparing the test sample response to the response obtained with the reference standard.

Data were analyzed using parallel line analysis. The controlled spreadsheet calculates relative potency with 95% confidence limits for the control and each test sample compared to the reference standard. The spreadsheet calculated relative potency by constructing an Analysis of Variance (ANOVA) table for the reference standard versus control and test samples. Once 3 valid determinations were obtained from 3 independent assays for a sample, a weighted mean result was calculated as per USP <111> using the controlled spreadsheet.

Results are set forth in FIG. 4.

What is claimed:

1. An antigen binding protein comprising SEQ ID NO: 3 wherein said antigen binding protein reduces binding of EGFR to EGF.

2. The antigen binding protein of claim 1, wherein said antigen binding protein is a monoclonal antibody or fragment thereof.

3. The antigen binding protein of claim 1, wherein said antigen binding protein is a human antibody, a humanized antibody, a chimeric antibody, a multispecific antibody, or fragment thereof.

4. The antigen binding protein of claim 3, wherein said antibody is a human antibody.

5. An antigen binding protein comprising SEQ ID NO: 4 wherein said antigen binding protein reduces binding of EGFR to EGF.

6. The antigen binding protein of claim 5, wherein said antigen binding protein is a monoclonal antibody or fragment thereof.

7. The antigen binding protein of claim 5, wherein said antigen binding protein is a human antibody, a humanized antibody, a chimeric antibody, a multispecific antibody, or fragment thereof.

8. The antigen binding protein of claim 5, wherein said antibody is a human antibody.

9. An antigen binding protein comprising the region spanning CDRs 1-3 of SEQ ID NO: 3 wherein said antigen binding protein reduces binding of EGFR to EGF.

10. An antigen binding protein comprising the region spanning CDRs 1-3 of SEQ ID NO: 4 wherein said antigen binding protein reduces binding of EGFR to EGF.

11. An anti-EGFR antibody having a point mutation at position 92 of SEQ ID NO:2 wherein said point mutation is a glutamic acid residue wherein said antigen binding protein reduces binding of EGFR to EGF or an aspartic acid residue.

12. A pharmaceutical composition comprising at least one antigen binding protein according to any one of claims 1, 5, or 9-11, and a pharmaceutically acceptable excipient.

13. The pharmaceutical composition of claims 1, 5, or 9-11 further comprising radioisotope, radionuclide, a toxin, a therapeutic agent, or a chemotherapeutic agent.

* * * * *

SEQUENCE LISTING

<160> NUMBER OF SEQ ID NOS: 10

<210> SEQ ID NO 1
<211> LENGTH: 445
<212> TYPE: PRT
<213> ORGANISM: Homo Sapiens
<220> FEATURE:
<221> NAME/KEY: MISC_FEATURE
<223> OTHER INFORMATION: Panitumumab heavy chain (gamma) amino acid
      sequence, (including Fc Portion)

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205
```

```
Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 2
<211> LENGTH: 214
<212> TYPE: PRT
<213> ORGANISM: Homo sapiens
<220> FEATURE:
<221> NAME/KEY: MISC_FEATURE
<223> OTHER INFORMATION: Panitumumab light chain (kappa) amino acid
      sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 214
<212> TYPE: PRT
<213> ORGANISM: Homo sapiens
<220> FEATURE:
<221> NAME/KEY: MISC_FEATURE
<223> OTHER INFORMATION: Panitumumab light chain (kappa) amino acid
      sequence with "E" mutation

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Glu His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 4
<211> LENGTH: 214
<212> TYPE: PRT
<213> ORGANISM: Homo sapiens
<220> FEATURE:
```

```
<221> NAME/KEY: MISC_FEATURE
<223> OTHER INFORMATION: Panitumumab Light Chain (Kappa) amino acid
      sequence with "N" mutation

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asn His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 9
<212> TYPE: PRT
<213> ORGANISM: Homo sapiens
<220> FEATURE:
<221> NAME/KEY: MISC_FEATURE
<223> OTHER INFORMATION: Light chain kappa variable region CDR 3 amino
      acid sequence with "E" mutation

<400> SEQUENCE: 5

Gln His Phe Glu His Leu Pro Leu Ala
1               5

<210> SEQ ID NO 6
<211> LENGTH: 9
<212> TYPE: PRT
<213> ORGANISM: Homo sapiens
<220> FEATURE:
<221> NAME/KEY: MISC_FEATURE
<223> OTHER INFORMATION: Light chain kappa variable region CDR 3 amino
      acid sequence with "N" mutation

<400> SEQUENCE: 6

Gln His Phe Asn His Leu Pro Leu Ala
1               5

<210> SEQ ID NO 7
```

```
<211> LENGTH: 705
<212> TYPE: DNA
<213> ORGANISM: Homo sapiens
<220> FEATURE:
<221> NAME/KEY: misc_feature
<223> OTHER INFORMATION: Light chain (kappa) nucleic acid sequence with
      "92E" mutation

<400> SEQUENCE: 7
atgagggtcc ctgctcagct cctggggctc ctgctgctct ggctctcagg tgccagatgt      60
gacatccaga tgacccagtc tccatcctcc ctgtctgcat ctgtaggaga cagagtcacc     120
atcacttgcc aggcgagtca ggacatcagc aactatttaa attggtatca gcagaaacca     180
gggaaagccc ctaaactcct gatctacgat gcatccaatt tggaaacagg ggtcccatca     240
aggttcagtg aagtggatc tgggacagat tttactttca ccatcagcag cctgcagcct     300
gaagatattg caacatattt ctgtcaacac tttgagcatc tcccgctcgc tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacctgacg     600 ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 8
<211> LENGTH: 705
<212> TYPE: DNA
<213> ORGANISM: Homo sapiens
<220> FEATURE:
<221> NAME/KEY: misc_feature
<223> OTHER INFORMATION: Light chain (kappa) nucleic acid sequence with
      "92N" mutation

<400> SEQUENCE: 8
atgagggtcc ctgctcagct cctggggctc ctgctgctct ggctctcagg tgccagatgt      60
gacatccaga tgacccagtc tccatcctcc ctgtctgcat ctgtaggaga cagagtcacc     120
atcacttgcc aggcgagtca ggacatcagc aactatttaa attggtatca gcagaaacca     180
gggaaagccc ctaaactcct gatctacgat gcatccaatt tggaaacagg ggtcccatca     240
aggttcagtg aagtggatc tgggacagat tttactttca ccatcagcag cctgcagcct     300
gaagatattg caacatattt ctgtcaacac tttaatcatc tcccgctcgc tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacctgacg     600 ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 9
<211> LENGTH: 27
<212> TYPE: DNA
<213> ORGANISM: Homo sapiens
<220> FEATURE:
<221> NAME/KEY: misc_feature
<223> OTHER INFORMATION: Light chain kappa variable region CDR3 nucleic
      acid sequence with "E" mutation
```

```
<400> SEQUENCE: 9
caacactttg agcatctccc gctcgct                                              27

<210> SEQ ID NO 10
<211> LENGTH: 27
<212> TYPE: DNA
<213> ORGANISM: Homo sapiens
<220> FEATURE:
<221> NAME/KEY: misc_feature
<223> OTHER INFORMATION: Light chain kappa variable region CDR3 nucleic
      acid sequence with "N" mutation

<400> SEQUENCE: 10
caacacttta atcatctccc gctcgct                                              27
```